(12) United States Patent
Zhen

(10) Patent No.: US 10,611,847 B2
(45) Date of Patent: Apr. 7, 2020

(54) ABCG2 MONOCLONAL ANTIBODY AND USES THEREOF

(71) Applicant: PEKING UNIVERSITY, Beijing (CN)

(72) Inventor: Hongying Zhen, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 0 days.

(21) Appl. No.: 16/333,532

(22) PCT Filed: Sep. 13, 2017

(86) PCT No.: PCT/CN2017/101549
§ 371 (c)(1),
(2) Date: Mar. 14, 2019

(87) PCT Pub. No.: WO2018/050066
PCT Pub. Date: Mar. 22, 2018

(65) Prior Publication Data
US 2019/0248912 A1 Aug. 15, 2019

(30) Foreign Application Priority Data

Sep. 14, 2016 (CN) .......................... 2016 1 0827464

(51) Int. Cl.
| A61K 39/395 | (2006.01) |
| C07K 16/28 | (2006.01) |
| C07K 14/47 | (2006.01) |
| A61K 31/00 | (2006.01) |
| A61P 35/00 | (2006.01) |
| A61K 39/00 | (2006.01) |

(52) U.S. Cl.
CPC .......... *C07K 16/2896* (2013.01); *A61K 31/00* (2013.01); *A61K 39/39558* (2013.01); *A61P 35/00* (2018.01); *C07K 14/47* (2013.01); *A61K 2039/505* (2013.01); *C07K 2317/24* (2013.01); *C07K 2317/34* (2013.01); *C07K 2317/56* (2013.01); *C07K 2317/622* (2013.01)

(58) Field of Classification Search
None
See application file for complete search history.

(56) References Cited

U.S. PATENT DOCUMENTS

| 2006/0233809 A1 | 10/2006 | Smith et al. |
| 2007/0141619 A1* | 6/2007 | Komatani ............... C07K 14/47 435/6.13 |

FOREIGN PATENT DOCUMENTS

| CN | 101724072 A | 6/2010 |
| CN | 104513297 A | 4/2015 |
| CN | 106432490 A | 2/2017 |
| WO | WO-0036101 A2 | 6/2000 |
| WO | WO-0069390 A2 | 11/2000 |
| WO | WO-2009061770 A2 | 5/2009 |

OTHER PUBLICATIONS

Yoshinaga et al., J. Biochem 2008; 143:593-601 (Year: 2008).*
De Genst et al., Dev Comp Innnnunol 2006; 30:187-98 (Year: 2006).*
Almagro & Fransson, Frontiers in Bioscience 2008; 13:1619-33 (Year: 2008).*
Yang, Guiping, et al.; "Preliminary Study of Inhibiting MM CSCs by ABCG2 Monoclonal Antibody in Combination with NPs-PTX in Vitro"; Chinese Journal of Immunology, 28(5), Dec. 31, 2012 (Dec. 31, 2012), pp. 385-388 (with English Abstract).
International Search Report (in English and Chinese) and Written Opinion of the Searching Authority (in Chinese) issued in PCT/CN2017/101549, dated Dec. 20, 2017, ISA/CN.
First Office Action regarding Chinese Application No. 201610827464.9 dated Mar. 22, 2019.

* cited by examiner

*Primary Examiner* — Meera Natarajan
(74) *Attorney, Agent, or Firm* — Harness, Dickey & Pierce, P.L.C.

(57) ABSTRACT

Disclosed are an ABCG2 monoclonal antibody having the effects for resisting against tumors and for reversing drug resistance of the tumors, and uses thereof in novel tumor resisting drugs. Also disclosed is a new antigen sequence, used for inducing generation of a monoclonal antibody or a polyclonal antibody for the ABCG2. In addition, disclosed is a hybridoma for generating the ABCG2 monoclonal antibody having the effects for resisting against tumors and for reversing drug resistance of the tumors.

10 Claims, 17 Drawing Sheets

Specification includes a Sequence Listing.

ABCG2 MONOCLONAL ANTIBODY AND USES THEREOF

This is a US National Phase application based upon PCT Application No. PCT/CN2017/101549, filed Sep. 13, 2017, which claims priority to Chinese Patent Application No. 201610827464.9, filed Sep. 14, 2016, the disclosures of which are hereby incorporated by reference in their entirety.

FIELD

The present invention relates to the field of molecular biology and oncology, specifically to an ABCG2 monoclonal antibody and uses thereof. Further, the present invention relates to an ABCG2 monoclonal antibody having antitumor and tumor drug resistance reversal effects, and uses thereof in novel tumor resisting drugs. The present invention also relates to a new antigen sequence, used for inducing generation of a monoclonal antibody or a polyclonal antibody for the ABCG2. In addition, the present invention relates to a hybridoma for generating the ABCG2 monoclonal antibody having antitumor and tumor drug resistance reversal effects.

BACKGROUND

Multidrug resistance (MDR) refers to a resistance to one type of drug as well as to other antitumor drugs with different structures and different targets. Its development may exist before chemotherapy (i.e. intrinsic resistance), or may develop during chemotherapy (i.e. acquired resistance). So far, the understanding of the mechanism of drug resistance is still very limited, increasing the outflow rate of anticancer drugs from tumor cells through the ATP-binding cassette (ABC) transport superfamily on the cell membrane is one of the most important mechanism. The ABC family is a group of transmembrane protein with ATP binding regions for transporting substrate in one direction, which performs membrane transport of multiple molecules by active transport. Three of the family members ABCB1/p-gp (p-glycoprotein, P-gp), ABCC1/MRP1 (Multidrug Resistance-associated Protein 1, MRP) and ABCG2/BCRP (Breast Cancer Resistance Protein, BCRP) are highly expressed in tumors with drug resistance (FIG. 1-1). By reducing the concentration of antitumor drugs in the cells, or redistributing antitumor drugs within the cells, these transmembrane proteins cause the development of drug resistance of tumor cells.

ABCG2/BCRP/MXR ABCG2 belongs to the G subfamily of the ABC transport protein family, has 655 amino acid residues and a molecular weight of 72 kD. It is localized on the cell membrane, has an ABC family characteristic hydrophilic motif at 1-400 residues, and has unique structural features: (1) consisting of one ATP-binding domain and hydrophobic carboxy-terminal transmembrane region with six alpha-helical transmembrane structures, which belongs to the half transport protein (McDevitt C A, Collins R F, Conway M, et al. Purification and 3D structural analysis of oligomeric human multidrug transporter ABCG2. Structure, 2006, 14(11):1623-1632); (2) localized on the cell membrane although belong to the half transporter; (3) the ATP-binding domain of ABCG2 is localized at the N-terminal while the transmembrane domain is localized at the C-terminal, and is structurally distinct from other subfamily transporters such as P-gp and MRP1 (FIG. 1-2); (4) a functional ABCG2 transporter requires two or more nucleotide binding domains and transmembrane domains to form a substrate transfer channel (Cheffer G L, Maliepaard M, Pijnenborg A C, et al. Breast cancer resistance protein is localized at the plasma membrane in mitoxantrone- and topotecan-resistant cell lines. Cancer Res, 2000, 60(10): 2589-2593). Therefore, ABCG2, as a semi-transporter, is likely to function as a homodimer or oligomer. Due to the specific structure of ABCG2, it is determined that the drug resistance mediated by ABCG2 is different from those of p-gp and MRP1.

Tumor drug resistance mediated by ABCG2 belongs to the intrinsic resistance. Researchers have isolated the cell components expressing ABCG2 from stem cells and tumor cell lines. The isolated cells have a stem cell-like phenotype, and resistant to the antitumor drugs mitoxantrone, doxorubicin, rubidomycin and topotecan (Kenneth K W and Fu L W. Multidrug resistance transporters-roles in maintaining cancer stem-like cells. Stem Cells in Clinic and Research. Chapter 30, 720-746, edited by Ali Gholamrezanezhad, ISBN 978-953-307-797-0, Published: Aug. 23, 2011 under CC BY-NC-SA 3.0license; Tan B, Piwnica-Worms D, and Ratner L, Multidrug resistance transporters and modulation. Curr Opin Oncol, 2000; 12,450-8.). ABCG2 is highly expressed in undifferentiated human embryonic stem cells (ESC) and cancer stem cells (CSC) (Kenneth K W and Fu L W. Multidrug resistance transporters-roles in maintaining cancer stem-like cells. Stem Cells in Clinic and Research. Chapter 30, 720-746, edited by Ali Gholamrezanezhad, ISBN978-953-307-797-0, Published: Aug. 23, 2011 under CC BY-NC-SA 3.0license; Apati A, Orban T I, Varga N, Nemeth A, Schamberger A, Krizsik V, Erdelyi-Belle B, Homolya L, Varady G, Padanyi R, Karaszi E, Kemna E, Nemet K, Sarkadi B. High level functional expression of the ABCG2 multidrug transporter in undifferentiated human embryonic stem cells. Biochim Biophy Acta, 2008, 1778 (12), 2700-2709), indicating that it has protective effects on ESC and CSC. Therefore, the CSC intrinsic drug resistance mediated by ABCG2 can be used as a target for CSC.

ABCG2 has important physiological functions in human body, which is characterized by blocking the permeability of drugs and toxins via expressing on the capillary endothelium of the blood-brain barrier and the placental barrier; the expression on the polar surface of small intestinal mucosal cells and colonic epithelial cells is associated with restricted absorption; the expression in liver and kidney tissues is associated with the elimination of drugs and toxins. ABCG2 acts as a multidrug resistance regulatory protein in breast cancer, colon cancer, small cell lung cancer, ovarian cancer, gastric and intestinal cancer, and malignant melanoma (Kathawala R J, Gupta P, Ashby C R Jr, Chen Z S. The modulation of ABC transporter-mediated multidrug resistance in cancer: A review of the past decade. Drug Resist Updat. 2015 January; 18C:1-17.doi:10.1016/j.drup; Shukla S, Ohnuma S, Ambudkar S V. Improving cancer chemotherapy with modulators of ABC drug transporters. Curr Drug Targets. 2011, 12(5), 621-30). The substrate of ABCG2 includes organic anion conjugate, nucleoside analogue, organic dye, tyrosine kinase inhibitor, anthracyclines, camptothecin-derived topoisomerase I inhibitor, methotrexate, flavonoid antineoplastic agents, etc. (Shukla S, Ohnuma S, Ambudkar S V. Improving cancer chemotherapy with modulators of ABC drug transporters. Curr Drug Targets. 2011, 12(5), 621-30). By inhibiting the expression of ABCG2 during tumor therapy, the efficacy of doxorubicin and mitoxantrone in breast cancer and irinotecan (camptothecin) in advanced colon cancer can be enhanced.

The Problems Currently Facing

Looking for drugs that effectively reverse ABCG2-mediated multidrug resistance has been a hot area in drug research and development (Assaraf Y G. The role of multidrug resistance efflux transporters in antifolate resistance and folate homeostasis. Drug Ressist Update, 2006, 9(4): 227). Despite years of research, potential multidrug resistance reversal agents have not yet been available, the reasons for that may be: first, most of the available multidrug resistance inhibitors are small molecular compounds, which are all based on the regulation of the transport function of ABCG2. These multidrug resistance reversal agents, which have good in vitro regulatory effects, produce strong toxicity and side effects after entering complex human environment due to the changes in the metabolic pathways of antitumor drugs (Kathawala R J, Gupta P, Ashby C R Jr, Chen Z S. The modulation of ABC transporter-mediated multidrug resistance in cancer: A review of the past decade. Drug Resist Updat. 2015 January; 18C:1-17. doi:10.1016/j.drup). Second, there are few specific inhibitors against ABCG2, and some small molecule compounds are both inhibitors of ABCG2 and p-gp. Third, in recent years, various kinase inhibitors have been used in researches of reversing ABCG2-mediated multidrug resistance, which have a good in vitro effect of reversing drug resistance, but no clinical trials have been conducted. However, the tyrosin kinase inhibitors themselves produce drug resistance during the treatment of tumors, making the multidrug resistance developed in tumor more complicated.

In the study of antibody reversal of tumor drug resistance targeting ABCG2, by direct binding of antibodies to ABCG2 protein expressed on the tumor cell membranes, the drug efflux may be specifically blocked, and the drug accumulation effect may be increased. Currently, there is no domestic or foreign detailed report about that, and it is a new target for antibody drugs. Therefore, the research and development of antibodies targeting ABCG2 should have better potential application value in tumor treatments, which reflects in a better interpretation of mechanism of ABCG2-mediated multidrug resistance of tumor as well as efficient and specific blocking of ABCG2-mediated tumor intrinsic resistance, by targeting CSC, inhibiting tumor growth.

Taking into account the above factors, the present disclosure develops a monoclonal antibody, which targets ABCG2, capable of reversing ABCG2-mediated tumor drug resistance; in addition, a research of application in terms of tumor treatment and characterization of the antibody is conducted to complete the present disclosure.

SUMMARY

The present disclosure provides an antigen sequence consisting of the sequence set forth in SEQ ID NO: 1. Or, a composition comprising the antigen sequence.

In another embodiment, the present disclosure provides three ABCG2 monoclonal antibodies that have both antitumor and tumor drug resistance reversal effects, and in another embodiment, the present disclosure provides three monoclonal antibodies respectively produced by the hybridomas deposited at China General Microbiological Culture Collection Center (CGMCC) with an accession number 12653 on Jun. 16, 2016, and the hybridoma deposited at China General Microbiological Culture Collection Center (CGMCC) with an accession number 14683 and 14684 on Sep. 5, 2017; wherein the address of China General Microbiological Culture Collection Center (CGMCC) is No. 1 Beichen West Road, Chaoyang District, Beijing, China.

In one embodiment, the present disclosure provides an antibody produced by the hybridoma with an accession number of CGMCC12653, having the light chain variable region sequence set forth in SEQ ID NO: 2 and the heavy chain variable shown in SEQ ID NO: 3; and an antibody ABCG2-PKU1-1 produced by the hybridoma with an accession number of CGMCC14683, having the light chain variable region sequence set forth in SEQ ID NO: 11 and the heavy chain variable region sequence set forth in SEQ ID NO: 12. Further, the ABCG2-PKU1 and ABCG2-PKU1-1 antibodies are conjugated to an anticancer drug, the anticancer drug is selected from the group consisting of cisplatin, doxorubicin, mitoxantrone, 5-fluorouracil, temozolomide, flavopiridol, or a mixture thereof.

In one embodiment, the present disclosure provides an engineered antibody comprising the light chain variable region sequence set forth in SEQ ID NO: 2 or ID NO: 11 and the heavy chain variable region sequence set forth in SEQ ID NO: 3 or ID NO: 12. The engineered antibody may be a humanized antibody or may be further engineered with a cancer therapeutic drug.

In some embodiments, the present disclosure provides an isolated antibody variant having one, two, three or more amino acid substitutions at conservative positions of the heavy chain variable region sequence set forth in SEQ ID NO: 3 or ID NO: 12 and the complementarity determining region of the light chain variable region sequence set forth in SEQ ID NO: 2 or ID NO: 11.

In one embodiment, the present disclosure provides a composition comprising the monoclonal antibody of the present disclosure, or comprising the engineered antibody of the present disclosure, optionally, the composition further comprises a pharmaceutically acceptable excipient.

In one embodiment, the present disclosure provides a hybridomas deposited at China General Microbiological Culture Collection Center (CGMCC) with an accession number 12653 on Jun. 16, 2016, and a hybridoma deposited at China General Microbiological Culture Collection Center (CGMCC) with an accession number 14683 and 14684, respectively, on Sep. 5, 2017; wherein the address of China General Microbiological Culture Collection Center (CGMCC) is No. 1 Beichen West Road, Chaoyang District, Beijing, China.

In another embodiment, the present disclosure provides a method of treating a disease comprising using the monoclonal antibody of the present disclosure or the engineered antibody of the present disclosure; optionally, it further comprises administering in combination with a cancer therapeutic drug.

In one embodiment, the present disclosure provides a use of the monoclonal antibody of the present disclosure or the engineered antibody of the present disclosure for the manufacture of a drug in treatment of a cancer: lung cancer, breast cancer, colon cancer, liver cancer, pancreatic cancer, glioma, gastric cancer, bladder cancer, cervical cancer, prostate cancer, ovarian cancer, chorionic epithelioma, malignant teratoma and leukemia, and lung cancer resistant to cisplatin, breast cancer resistant to doxorubicin, flavopiridol, 5-fluorouracil and mitoxantrone, and colon cancer resistant to flavopiridol and mitoxantrone; preferably, the cancer is lung cancer. Furthermore, the cancer includes, but is not limited to, the foregoing types of cancer.

In another embodiment, the present disclosure provides a use of the antigen sequence of the present disclosure or a use of a composition containing the antigen in the preparation of an ABCG2 monoclonal antibody or polyclonal antibody.

In some embodiments, the antibody of the present disclosure can be used for the detection of ABCG2, the detection may be either an enzyme-linked immunosorbent assay (ELISA) or a radioimmunoassay (RIA) or chemiluminescence immunoassay (CLIA), for example, electrochemiluminescence immunoassay (ECLI). Preferably, the detection is enzyme-linked immunosorbent assay (ELISA).

The term "antibody" as used herein refers to an immunoglobulin molecule that specifically binds to or immunologically responsive to a particular antigen, which includes polyclonal, monoclonal, genetically engineered, and otherwise modified forms of the antibody, the form of which includes but not limited to chimeric antibodies, humanized antibodies, heteroconjugated antibodies (e.g., di-, tri-, and tetra-specific antibodies, diabody, triabody, and tetrabody); and antigen-binding fragments thereof include, for example, Fab', F(Ab')2, FAB, FV, rIgG and scFv fragments. The antibody may include chimeric, primatized, humanized or human antibodies. The antibodies used in connection with the present disclosure may be generated using a variety of techniques known in the art including the use of animal immunization, hybridoma, recombinant and phage display techniques, or combinations thereof.

In some embodiments, the antibody used in the present disclosure may be a labeled antibody. The term "labeled" as used herein refers to coupling an antibody to a therapeutic drug to facilitate treatment. The therapeutic drug includes cisplatin, doxorubicin, mitoxantrone, 5-fluorouracil, temozolomide and flavopiridol. The therapeutic drug may be coupled or conjugated to the antibody (or fragment thereof) directly or indirectly by an intermediate (e.g., a linker known in the art) using techniques known in the art. The monoclonal antibody of the present disclosure may also be used in conjunction with a suitable radioactive material, the specific radioactive material includes $^{125}$I, $^{131}$I, $^{111}$In or $^{99}$Tc.

In another aspect, the monoclonal antibody provided by the present disclosure may be used in combination with other drugs, preferably in combination with cancer treatment drugs. In some embodiments, the monoclonal antibody of the present disclosure is used in the treatment of early-stage cancer, intermediate or advanced cancer.

In some embodiments, the monoclonal antibody of the present disclosure is administered to a mammal. Preferably, the subject is human, such as, but not limited to, a European population, a North American population, and/or a Chinese population.

Information Regarding Deposit

The present disclosure provides three monoclonal antibodies, the deposit institution: China General Microbiological Culture Collection Center (CGMCC); address: No. 1 Beichen West Road, Chaoyang District, Beijing, China; a deposit with a deposit date of Jun. 16, 2016, a biological source number of 266CT10.5.1 and an accession number CGMCC12653; a deposit with a deposit date of Sep. 5, 2017, biological source numbers of 266CT10.5.4 and 266CT15.3.2 and accession numbers of CGMCC14683 and CGMCC14684, respectively.

BRIEF DESCRIPTION OF DRAWINGS

FIG. 1-2 shows a structural pattern diagram of ABC transport protein. ABCG2 exists as a half transporter on the cell membrane, while MDR1/p-gp is in the form of a dimer, and MRP1 is in the form of a trimer. Each half transporter is a protein spanning the membrane six times. The protein has an amino terminal (N) and a carboxy terminal (C). Usually, the ATP binding site (ABC) is at the carboxy terminal, but it is different that the ATP binding site of ABCG2 is at the N terminal. ABCG2 generally exists as a homodimer.

FIG. 1-3 shows that ABCG2 forms a functional tetramer on the cell membrane. ABCG2 protein is synthesized in the endoplasmic reticulum, and after correct folding and glycosylation, it enters the Golgi apparatus and forms a homodimer via disulfide bond. A single ABCG2 first forms a dimer on the plasma membrane. Recent crystal structure studies have shown that the functional tetrameric complex is composed of four BCRP/ABCG2 dimers, which are degraded by lysosomes after functioning, while the proteins that are not normally folded enter the proteasome system for degradation.

FIG. 1-4 shows a topological pattern diagram of ABCG2. Crystal structure studies have shown that the functional tetrameric complex consists of four dimers of BCRP/ABCG2. Its half transporter N-terminal binding domain (NBD) has 395 amino acids and located in the cytoplasm and the C-terminal binding domain (MSD) is located at amino acids 396-655. Amino acids 415-450 form the first transmembrane domain outside the cell, amino acids 497-505 form the second transmembrane domain outside the cell, and amino acids 585-627 form the third transmembrane domain outside the cell. The asparagine at position 596 undergoes N-linked glycosylation and forms a disulfide bond between 592 and 608 cysteines that maintains its own stability. The solid circle marked by numbers represents single nucleotide variations in the genome.

FIG. 1-5 shows that the antigen sequence is at position 618-633, and the thereby produced ABCG2-PKU1, ABCG2-PKU1-1 and ABCG2-PKU2 antibodies can act on the functional domain formed by the ABCG2 protein dimer so as to disrupt the ABCG2 protein dimerization.

FIG. 2 shows the identification of immune sera by Western Blot. In the image, the vertical 3 rows of numbers 250, 130, 95, 72 represent molecular weight markers, the lanes of the molecular weight marker are not numbered. There are 4 lanes between each two rows of molecular weight markers, from left to right numbered as lanes 1-12, and the second row is numbered in turn as lanes 13-24. Only the antibody produced by mice immunized with the right leg (coded MS1148) could bind to the 72 KD (lanes 3, 7, 11, 15, 19, 22) ABCG2 protein expressed on the surface of K562, A549, NCI-H460, WiDR, MDA-MB435 and HepG2 tumor cells. While the antibody produced by other immuned sites, left ear, right ear, and unlabeled mice, (lanes 1, 2, 4, 5, 6, 8, 9, 10, 12, 13, 14, 16, 17, 18, 20, 21, 23, 24) could not recognized ABCG2 protein at position 72KD expressed on the surface of these tumor cells.

FIG. 3 rescreening secondary subclones identified by Western Blot. Vertical lanes marked by numbers are molecular weight marker without lane number, lanes 1-10 were clone numbers 1-10 CT10.5(1-5) and 266CT15.3(1-5). WB results show the culture supernatants of clones 266CT10.5 (1-4) and 266CT15.3(5) can hybridize with lysates from WiDR and NCI-H460 cells and showed clear band at 72KD (lanes 11-14, 20 and 31-35, 40), while the bands of 266CT10.5(5) and 266CT15.3(1-4) clones were weak (lanes 15-19 and 36-39). The bands from the lysates of K562 and A549 cells were weaker at 72 KD (lanes 1-10 and 21-30). It indicated that the clones 266CT10.5(1-4) and 266CT15.3(5) were positive clones.

FIG. 4 shows the results of Western Blot identification of ascites antibodies produced by clone number 266CT10.5.1 and clone number 266CT10.5.4 hybridoma cells. FIG. 4-1 is the identification of the clone number 266CT10.5.1, the vertical labels 72, 55, 36, and 28 are molecular weight markers, between each of the two molecular weight marker are lanes in which ascites was diluted according to the ratios of 1:500, 1:1000, 1:2000, 1:4000, and then respectively hybridized with HepG2, K562 and NCI-H460 cell lysates. At 72 KD position, HepG2 cells showed strong hybridization bands in lanes 1-4, both K562 and NCI-H460 cells showed hybridization bands from strong signal to weak signal in lanes 1-3. FIG. 4-2 is the identification of the clone number 266CT10.5.4, the vertical labels 95, 72, 55, 36, 28 are molecular weight markers. In the lanes of HepG2, K562 and NCI-H460 cells, cell lysate was in lane 1 which showed a strong band at 72 KD; no cell lysate was added to lane 2, there was no hybridization band at 72 KD; and lane 3 was a molecular weight marker.

FIG. 5 detection of mRNA expression levels in drug-resistant cell lines. The mRNA expression levels of the drug-resistant genes ABCG2, p-gP and MRP1 of the drug-resistant strains MCF7/FLV1000 and SW480/MX2500 were all improved compared with breast cancer cell MCF7 and colon cancer cell SW480, particularly, the mRNA expression level of ABCG2 was improved by more than 5 times. The MCF-FLV1000/MCF7 cells in the figure represents the comparison of the drug-resistant strain FLV1000/MCF7 with the non-resistant strain MCF, and the SW480-MX2500/SW480 cells in the figure represents the comparison of the drug-resistant strain MX2500/SW480 with the non-resistant strain SW480.

In FIG. 8A-F, the solid line represents the control group without drug treatment, the dotted line represents the treatment group added mitoxantrone, the square-dotted line represents the ABCG2-PKU1 antibody treated group, the short-dashed line represents the ABCG2-PKU2 antibody treated group, the dashed-dotted line is the mitoxantrone+ABCG2-PKU1 antibody treated group, and the long-dashed line is the mitoxantrone+ABCG2-PKU2 antibody treated group. The result shows that the ABCG2-PKU1 antibody and ABCG2-PKU2 antibody enhanced the sensitivity of mitoxantrone, in particular, the effect of ABCG2-PKU2 antibody on enhancing sensitivity of mitoxantrone was more obvious in ABCG2 high expression MCF7/Mitoxantrone drug-resistant cells. In Figures I-L, the thick solid line represents the control group without drug treatment, the dotted line represents the treatment group added mitoxantrone, the square-dotted line represents the ABCG2 antibody treated group, the short-dashed line represents the ABCG2-PKU1 antibody treated group, the dashed-dotted line is the ABCG2-PKU1-1 antibody treated group, the long-dashed line is the ABCG2-PKU2 antibody treated group, the long-dashed-dotted line is the ABCG2 antibody+mitoxantrone treated group, the long-dashed-dotted-dotted line is the ABCG2-PKU1 antibody+mitoxantrone treated group, the medium solid line is the ABCG2-PKU1-1 antibody+mitoxantrone treated group, and the thin solid line is ABCG2-PKU2 antibody+mitoxantrone treated group. The result shows that the ABCG2 antibody (commercial antibody BXP-21), ABCG2-PKU1 antibody, ABCG2-PKU1-1 antibody and ABCG2-PKU2 antibody have effect on enhancing sensitivity of mitoxantrone, in particular, the effect of ABCG2-PKU1-1 antibody on enhancing sensitivity of mitoxantrone was more obvious in ABCG2 high expression MCF7/Mitoxantrone drug-resistant cells, and effect was more than one time better than that of ABCG2-PKU1. The effects of ABCG2 antibody and ABCG2-PKU2 antibody were relatively weak.

FIG. 9-1, A is breast cancer cell MCF7, B is doxorubicin (ADM)-resistant strain MCF7/ADM; FIG. 9-2, A is lung cancer cell A549, B is cisplatin (CIS)-resistant strain A549/CIS. Wherein Curve-1 is the group of cells without drug treatment, Curve-2 is the group of cells treated with ABCG2-PKU1 antibody, and Curve-3 is the group of cells treated with ABCG2-PKU1 antibody+MTX. The result shows that ABCG2-PKU1 antibody increased the accumulation of MTX in tumor drug-resistant cells (Curve-3). FIG. 9-3 is the comparison of antibodies ABCG2-PKU1, ABCG2-PKU1-1 and ABCG2-PKU2 on the accumulation of mitoxantrone (MTX) in cells, wherein Curve-1 is the group of cells without drug treatment, Curve-2 is the group of cells treated with MTX, Curve-3 is the group of cells treated with ABCG2 inhibitor FTC+MTX, Curve-4 is the group of cells treated with ABCG2-PKU1 antibody+MTX, Curve-5 is the group of cells treated with ABCG2-PKU1-1 antibody+MTX, Curve-6 is the group of cells treated with ABCG2-PKU2 antibody+MTX. The result shows that the effect of the ABCG2-PKU1-1 antibody on increasing the accumulation of MTX in tumor drug-resistant cells (Curve-5) was slightly stronger than that of ABCG2 inhibitor FTC (Curve-3), the effect of ABCG2-PKU1 antibody (Curve-4) ranked second, and the effect of ABCG2-PKU2 antibody (Curve-6) was relatively weak.

FIG. 10C shows that all the tumor volumes decreased with certain degrees after antibody treatment compared with the control group. In FIG. 10D, the line is the control group, the dotted line is ABCG2 antibody group, the square-dotted line is ABCG2-PKU1 antibody group, the short-dashed line is ABCG2-PKU1-1 antibody group, and the dashed-dotted line is ABCG2-PKU2 antibody group. Compared with the control group without administration, ABCG2 antibody group, ABCG2-PKU1 antibody group and ABCG2-PKU2 antibody group, the ABCG2-PKU1-1 antibody group has the strongest effect on reducing the transplanted tumor volume, the ABCG2-PKU1 antibody group ranked second, the ABCG2 and ABCG2-PKU2 antibody groups were slightly weaker.

FIGS. 11A and C are lung cancer cell A549, B and D are drug-resistant strain A549/cis. In Figures A and B, within 72 hours of antibody treatment, there was not substantially cell apoptosis. The percentage of apoptotic cells was counted by histograms of the lower images in FIGS. 11A and B, and in 11C and D. In Figures C and D, within 72 hours of antibody treatment of ABCG2-PKU1, ABCG2-PKU1-1, and ABCG2-PKU2 respectively, there was not substantially cell apoptosis, indicating that apoptosis is not the main mechanism by which these three ABCG2-PKU antibodies act on tumor cells.

DETAILED DESCRIPTION

Figure 1:
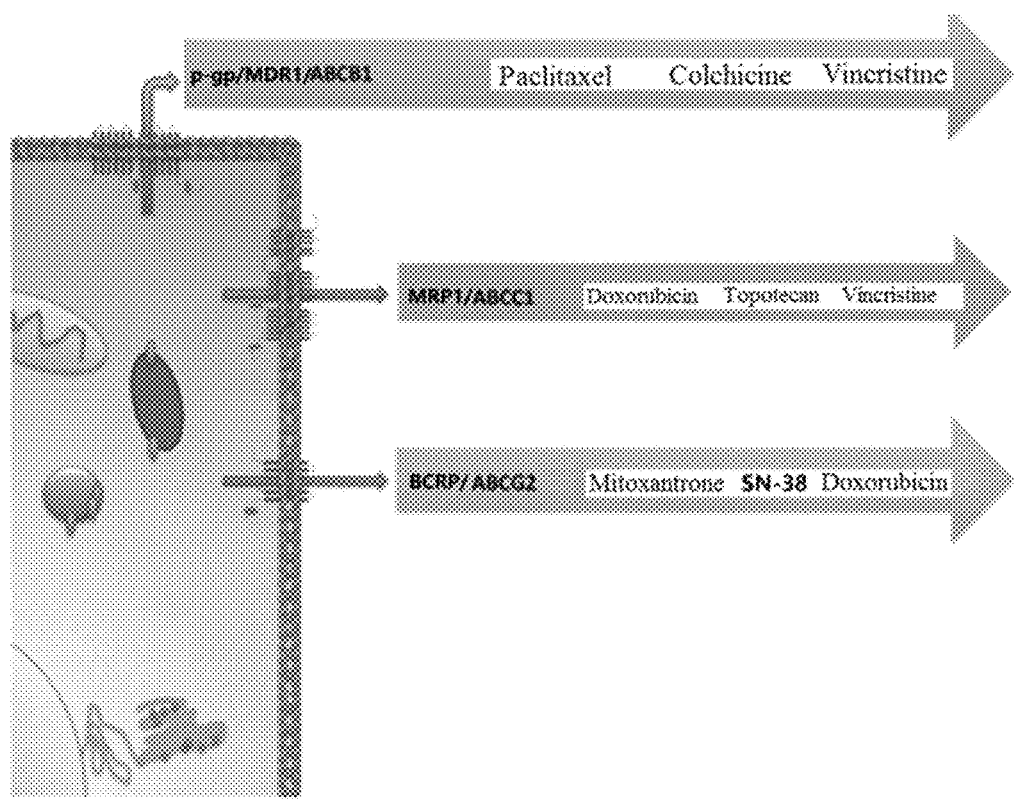
FIG. 1-1 shows the anticancer drug as a substrate for the MDR-ABC transporter, the proteins encoded by the main three drug resistance genes ABCB1, ABCC1 and ABCG2 expressed by tumor cells are p-gp, MRP1 and ABCG2. The substrates of p-gp are paclitaxel, colchicine, vincristine, etc.; the substrates of MRP1 are doxorubicin, topotecan, vincristine, etc.; and the substrates of ABCG2 are mitoxantrone, SN-38 and doxorubicin, etc. Each drug resistance protein has its own substrate, which can overlap each other.

The development of drug resistance greatly increases the difficulty of tumor treatment. For many years, scientists have been striving to find drugs that effectively reverse tumor drug resistance, however, it is hard for traditional candidate compound reversing drug resistance to solve the problem of drug tolerance in clinical tumors treatment, which promotes the discovery of new drug targets as well as changing and innovating drug discovery model, and carrying out drug research to effectively reverse ABCG2-mediated tumor resistance.

In the study of antibody reversal of tumor drug resistance targeting ABCG2, by the direct binding of antibodies to ABCG2 protein expressed by the tumor cell membranes, drug efflux is specifically blocked and the drug accumulation effect is increased, making ABCG2 a new target for antibody drugs. Therefore, the research and development of antibody targeting ABCG2 should have better potential application value in tumor treatments, which reflects in a better interpretation of mechanism of ABCG2-mediated multidrug resistance of tumor as well as efficient and specific blocking of ABCG2-mediated tumor intrinsic resistance, by targeting CSC so as to inhibit tumor growth.

Since BCRP/ABCG2 is a half ABC transporter composed of a nucleotide binding domain (NBD) and a transmembrane domain (TMD). The N-terminal NBD includes the amino acid from 1 to 395, and the function is an ATP-binding region. The C-terminal TMD is from 396 to 655, which is a domain spanning the membrane six times, wherein the amino acids 415-450 form an extracellular loop domain between TM1 and TM2; amino acids 497-505 form an extracellular loop domain between TM3 and TM4; and amino acids 585-627 form the largest extracellular loop domain between TM5 and TM6. The ABCG2 dimer is formed via the disulfide bond of cysteine at position 603. Recent crystal structure studies have shown that the functional tetrameric complex is composed of four BCRP/ABCG2 dimers. Through the endoplasmic reticulum-Golgi pathway, BCRP is translocated to the cell membrane after synthesis, with N-linked glycosylation at asparagine at position 596. Due to the formation of a disulfide bond between cysteine at positions 592 and 608, which maintains its own stability, is the functional domain for forming ABCG2 homologous oligomeric complexes, it can be used as an antigen to reverse tumor drug resistance in tumor treatment. However, when we designed it as an immunizing antigen, we found that this amino acid sequence (positions 592-608) is not suitable as a good antigen. Therefore, we used the 15 amino acids of 618-633 as an antigenic polypeptide, and by multiple hybridoma technique, to obtain ABCG2-PKU1 antibody and ABCG2-PKU1-1 antibody.

Currently, available commercial ABCG2 antibodies are mainly: (1) BXP21, which is a murine monoclonal antibody targeting human ABCG2 amino acids 271-396, the subtype is IgG2a; (2) 5D3, which is a murine monoclonal antibody targeting recombinant human ABCG2 transfected into mouse 3T3 fibroblasts, the subtype is IgG2b; (3) B1, which is a murine monoclonal antibody targeting human ABCG2 amino acids 301-370, the subtype is IgG1; (4) 6D171 [sc-69988], which is a murine monoclonal antibody targeting human ABCG2 amino acids 271-396, the subtype is IgG1; (5) 1H2 [ab130244], which is a murine monoclonal antibody targeting purified human recombinant ABCG2 fragment expressed in E. coli, the subtype is IgG1; (6) BXP-34 [ab3379], which is a murine monoclonal antibody targeting ABCG2 overexpressed in MCF7 cells, the subtype is IgG1; (7) 3G8 [MA5-15853], which is a murine monoclonal antibody targeting purified human recombinant ABCG2 fragment expressed in E. coli, subtype is IgG1. Most of these antibodies target the N-terminal of ABCG2 protein, which is different from the antigenic determinants of ABCG2-PKU1 antibody and ABCG2-PKU1-1 antibody we used, wherein the antigenic determinants of 5D3, 1H2 and 3G8 are not clear. Since the N-terminal of ABCG2 protein is a nucleotide binding site, it does not affect the formation of ABCG2 dimer. Therefore, as shown in FIG. 1-5, the monoclonal antibodies ABCG2-PKU1 and ABCG2-PKU1-1 targeting ABCG2 of the present disclosure are the only ABCG2 monoclonal antibodies using 618-633 as an antigenic determinant and clearly targeting the extracellular loop domain formed between the C-terminal TM5 and TM6. By disrupting the formation of ABCG2 dimer via the disulfide bond of cysteine at position 603, the antibodies further disrupt the formation of ABCG2 homologous oligomeric complex. The present disclosure, for the first time, fundamentally eliminates the structure for ABCG2 protein homologous oligomeric complex which develops drug resistance, and has a breakthrough in the study of reversing tumor drug resistance.

To confirm that the obtained monoclonal antibodies ABCG2-PKU1 and ABCG2-PKU1-1 have the effect of reversing drug resistance, doxorubicin-resistant breast cancer MCF7/ADM cells and cisplatin-resistant lung cancer A549/cis cells, purchased from Chinese Academy of Medical Sciences were used according to the literature (Wang X Q, Ongkeko W M, Chen L, Yang Z F, Lu P, Chen K K, Lopez J P, Poon R T, Fan S T. Octamer 4 (Oct4) Mediates Chemotherapeutic Drug Resistance in Liver Cancer Cells Through a Potential Oct4-AKT-ATP-binding Cassette G2 Pathway, Hepatology. 2010 August; 52(2):528-39. doi: 10.1002/hep.23692). Antitumor drugs were used to induce breast cancer cell MCF7 and colon cancer cell SW480, respectively, to obtain strains resistant to antitumor drugs flavopiridol (FLU) and mitoxantrone (MTX), which were named breast cancer MCF7/FLV1000 cells and MCF7/MTX250 cells, and colon cancer SW480/MTX2500 cells resistant to mitoxantrone. The in vitro cytology experiments of Example 5 demonstrated that both ABCG2-PKU1-1 and ABCG2-PKU1 antibodies enhanced the antitumor effects of antitumor drug mitoxantrone against drug-resistant cells MCF7/FLV1000 and A549/cis and increased the accumulation of mitoxantrone in the drug-resistant cells MCF7/ADM and A549/cis, but the antibodies did not induce apoptosis of tumor cells or the drug-resistant cells. Therefore, the antibodies reversed the drug resistance of tumor cells by a non-apoptotic mechanism, and ABCG2-PKU1-1 has a better effect than ABCG2-PKU1. The nude mouse tumor-bearing experiment of Example 6 demonstrated that ABCG2-PKU1-1 and ABCG2-PKU1 antibodies strongly inhibited the tumorigenic effect of lung cancer A549 cells in vivo, and the antitumor effect of ABCG2-PKU1-1 was stronger than that of ABCG2-PKU1. It was speculated that these two antibodies might inhibit the self-renewal of tumor cells by acting on CSC, affect the tumor microenvironment by acting on mesenchymal stem cells, and further show the advantage of inhibiting tumor growth.

Taken together, ABCG2-PKU1-1 and ABCG2-PKU1 antibodies have a strong ability to reverse the development of tumor drug resistance, and as a new drug to be researched in the future, have an absolute advantage over all current preclinical and clinically entered drugs that reverse tumor drug resistance.

The present disclosure is illustrated below with reference to specific embodiments, the scope of protection of the present invention is not limited thereto.

Example 1: Preparation of Anti-ABCG2 Mouse Hybridoma Cell

1. Synthesis of Antigenic Peptide Sequence

According to the transmembrane sequence of ABCG2 on the cell surface, the antigenic polypeptide sequence was designed as TGEEYLVKQGIDLSP (SEQ ID NO: 1), which was localized at amino acid positions 618-633 of the carboxy terminal of ABCG2. The sequence was synthesized by Shanghai K E Biochem Co., Ltd. 10 mg of the polypeptide shown in SEQ ID NO: 1 was used as an immunizing antigen.

2. Polypeptide Coupling: The Antigenic Polypeptide Synthesized in Step 1 was Coupled by KLH Method (1) Coupling agent SMCC is a bifunctional coupling agent containing an active ester of N-hydroxysuccinimide (NETS) and maleimide, which can bond together compounds respectively containing a sulfhydryl group and an amino group. 5 mg of SMCC (amount for linking 10 antigen peptides) was dissolved in 0.5 ml of dimethyldiamide (DMF).

(2) 5 mg of hemocyanin KLH was added to a 25 ml round-bottom flask, 1×PBS (pH 7.2) was replenished to make a final protein concentration of 10 mg/ml.

(3) The well dissolved SMCC solution was slowly added dropwise to 10 mg/ml KLH protein system, stirred at room temperature for 1 hour.

(4) The solution was dialyzed against 1 L of 1×PBS (pH 7.4) at 4° C. for 6 hours to remove free SMCC.

(5) The dialyzed KLH protein was poured into a 50 ml centrifuge tube, the volume was determined by the scale of the centrifuge tube. Concentration of the protein after dialysis was calculated according to the amount of KLH protein added before the reaction, and then 2.5 mg of KLH-SMCC solution was transferred to a 5 ml centrifuge tube according to the concentration. For example, the amount of the KLH protein added before the reaction was 5 mg, and the volume of the KLH protein after dialysis was 1 ml, then the concentration of the KLH protein after dialysis was 5 mg/ml, 2.5/5=500 µl KLH-SMCC solution should be transferred to a 5 ml centrifuge tube.

(6) 10.0 mg of the antigenic polypeptide of step 1 was dissolved in 0.6 ml of 1×PBS (pH 7.2) solution. Note: 0.5 mg (100 µl) of antigenic peptide was used later for ELISA.

(7) Ellman reagent was used to detect the sulfhydryl group in polypeptide: 100 µl of Ellman reagent stock solution was added to a 96-well plate, and 10 µl of the polypeptide solution was added thereto, the ultraviolet absorption value was measured by a Nano spectrophotometer at λ=412 nm to be 0.17. Note: If the OD value was >0.15, the next step was performed; if the OD value was <0.15 and >0.05, polypeptide was replenished until the requirement was reached; if the OD value was <0.05, then returned to the peptide synthesis step for re-quality control. (Ellman reagent was used to detect free sulfhydryl groups, if the detection solution was yellow, it indicated that the sulfhydryl group of the Cys of the polypeptide was mostly in a free state; if the detection solution was not yellow, it indicated that the sulfhydryl group in the polypeptide Cys had been oxidized to form a dimer or multimer.)

(8) The polypeptide was added dropwise into a KLH-SMCC tube and mixed by a vertical mixer at room temperature for 4 hours.

(9) Ellman reagent was used to detect the sulfhydryl group in polypeptide: 100 µl of Ellman reagent stock solution was added to a 96-well plate, 10 µl of the cross-linked polypeptide solution was then added, the ultraviolet absorption value was measured by a Nano spectrophotometer at λ=412 nm to be 0.25. Note: The OD value <0.03 indicated that the cross-linking rate of the polypeptide and KLH protein had reached 80% or more; the OD value >0.03 then SMCC-activated KLH protein was replenished to continue cross-linking. If the Ellman reagent was yellow, it indicated that the coupling of the polypeptide to the KLH protein was incomplete; if the Ellman reagent was not yellow, it indicated that the polypeptide had all been coupled to the KLH protein.

(10) A coupled antigenic polypeptide was obtained.

3. Mouse Immunization (1) Four Balb/c mice of 8-9 weeks were subjected to immunoinjection at multiple sites using the polypeptide-conjugated antigen obtained in step 2 at a dose of 100 μg/site; subsequently, the immunization was boosted once every two weeks for 3 times at a dose of 50 μg/site; and on the day of the fourth immunization, blood was collected, 40 μl/time, once a week, and blood was collected four times in succession. Serum was separated and antibody titer was measured by indirect ELISA.

(2) ELISA Experiment

1) The polypeptide synthesized in the above step 1 was added as an antigen to a 96-well plate and incubated at room temperature overnight to form antigen coated solid phase; the plate was washed with PBS to remove unbound antigen and impurities; 3% BSA/PBS was added for blocking, and then washed with PBS to remove unbound BSA; 2) the diluted test serum (1:500-1:16000) was added to 0.05% Tween 20/PBS, at 37° C. for 2 hours; the specific antibody in the serum bound to the antigen on solid phase to form a solid phase antigen-antibody complex; the plate was washed with PBS, only the specific antibody remained on the solid phase carrier, and other components in the serum were washed off during the washing process; 3) enzyme-labeled anti-antibody was added, that is, IgG antibodies were detected with horseradish peroxidase-labeled anti-mouse IgG (1:5000); the antibody in the solid phase immune complex bound to the enzyme-labeled antibody, thereby indirectly labeled with enzyme; after washing, the amount of the enzyme on the solid phase was positively correlated with the amount of the antibody to be tested; 4) color development: 100 μl of substrate solution (0.015% $H_2O_2$; OPD, 2.5 mg/mL) was added, incubated at room temperature for 30 minutes, 100 μl of $H_2SO_4$ was then added to terminate the reaction; the detection wavelength of the microplate reader was 450 nm.

The OD 450 nm result of the ELISA is as shown in Table 1.

TABLE 1

| Dilution Factor | Immune Sites | | | |
| --- | --- | --- | --- | --- |
| | Left Ear | Right Ear | Right Leg | None |
| 1/1000– | 0.106 | 0.096 | 0.094 | 0.071 |
| 1/4000– | 0.095 | 0.096 | 0.085 | 0.084 |
| 1/500 | 2.148 | 2.326 | 2.258 | 2.178 |
| 1/1000 | 2.176 | 2.208 | 1.778 | 1.633 |
| 1/2000 | 2.055 | 2.059 | 1.844 | 1.436 |
| 1/4000 | 1.779 | 1.749 | 1.339 | 1.013 |
| 1/8000 | 1.585 | 1.689 | 1.213 | 1.006 |
| 1/16000 | 1.191 | 1.281 | 0.867 | 0.963 |

Positive criteria: 1:4000 OD value ≥1.

A total of 4 mice serum met the positive criteria by ELISA.

(3) Test Immune Serum by Western Blot

Figures 1, 2:
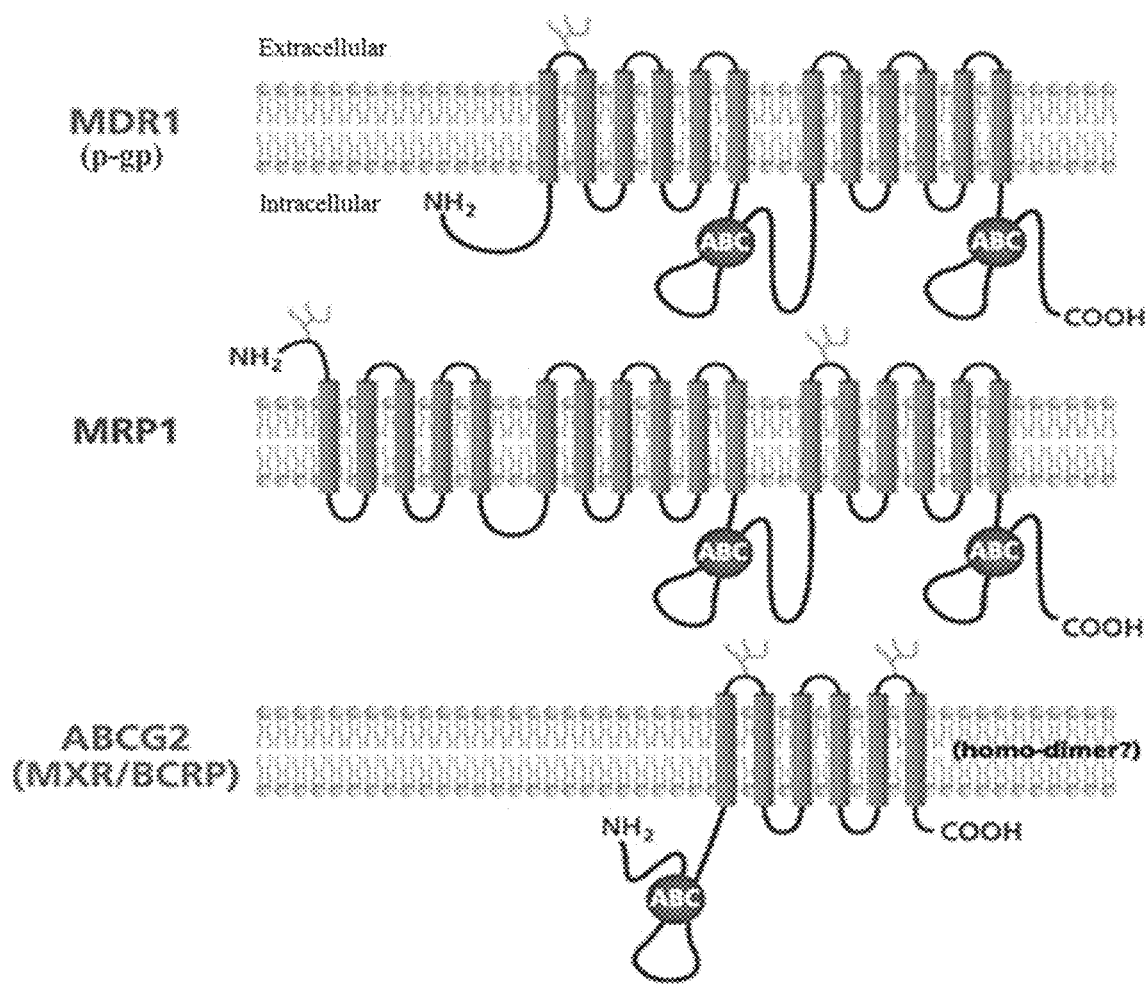

All cells used in the experiments were purchased from ATCC (U.S.). Proteins of K562, A549, NCL460, WiDR, MDA-MB435 and HepG2 tumor cells were extracted. First, the tumor cells were collected and the supernatant was removed after centrifugation. Lysis buffer (50 mM Tris (pH 7.4), 150 mM NaCl, 1% NP-40, 0.5% sodium deoxycholate) was added, and the lysed cells were resuspended, centrifuged at 4° C. for 50 minutes. After the protein concentration was measured, SDS-PAGE (SDS-polyacrylamide) electrophoresis was performed. Before membrane transfer, the PVDF membrane was immersed in a methanol solution, and then transferred to a transfer buffer for rinsing, and then membrane transfer was carried out. After transfer, the membrane was blocked in 5% milk/PBS at 4° C. overnight. The membrane was washed 3 times with TBST the next day. Then, the four groups of immune sera obtained after immunization of the foregoing mice (left ear, right ear, right leg and no label) were incubated with the membrane for 2 hours at room temperature. The membrane was washed 3 times with TBST, a commercial horseradish peroxidase-labeled secondary antibody (Pharmingen, 1:3,000) was added and incubated at room temperature for 1 hour, and then the signal was developed. The result is as shown in FIG. 2. The result indicated that only the antibody produced by mice immunized at the right leg (coded MS1148) could bind to (lanes 3, 7, 11, 15, 19, 22) ABCG2 protein (72KD) expressed on the surface of K562, A549, NCL-H460, WiDR, MDA-MB435 and HepG2 tumor cells. While the antibodies produced by mice with other immune sites, left ear, right ear, and unlabeled mice could not recognized (lanes 1, 2, 4, 5, 6, 8, 9, 10, 12, 13, 14, 16, 17, 18, 20, 21, 23, 24) ABCG2 protein (72KD) expressed on the surface of these tumor cells.

4. Cell Fusion, Clone Screening and Identification of IgG Subtype

It was found by the detection that only the antibody produced by No. MS1148 immunized at the right leg could bind to ABCG2 protein (72KD) expressed on the surface of K562, A549 and NCL-H460, WiDR, MDA-MB435 and HepG2 tumor cells. While the antibody produced by mice immunized at other immune sites, left ear, right ear, and unlabeled could not bind to ABCG2 protein (72KD) expressed on the surface of K562, A549 and NCL-H460, WiDR, MDA-MB435 and HepG2 tumor cells.

(1) Cell Fusion

1) Feeder Cell Preparation

Preparation of mouse peritoneal macrophages: the mice used were of the same strain as the immunized mice: 8-week old BaLb/c mice. The mice were sacrificed, immersed in 75% alcohol, disinfected for 3 to 5 minutes. The skin was cut with sterile scissors, and the peritoneum was exposed. 6-8 ml of medium was injected with a sterile syringe, rinsing was repeated, the rinsing solution was aspirated out, put into a 10 ml centrifuge tube, centrifuged at 1200 rpm for 5 minutes. The cell pellet was resuspended in medium containing 20% newborn calf serum (NCS) or fetal bovine serum (FCS). The number of cells was adjusted to $1\times10^5$/ml, and the cells were added to a 96-well plate, 100 μl/well. The plate was placed in a 37° C. $CO_2$ incubator.

2) Myeloma Cells

The myeloma cells SP2/0 were resuscitated two weeks before the fusion, and cultured in RPMI1640 medium containing 15% fetal calf serum at a maximum cell density of $10^6$/ml or less. The cells were subcultured at a 1:10 dilution to ensure the myeloma cells in a logarithmic growth phase, with a good morphology, and a viable cell count higher than 95%. The cells were passaged every 3 to 5 days. The doubling time of the cells was 16 to 20 hours.

3) Preparation of Spleen Cells

For the mice numbered MS1148, the spleen was taken to prepare a cell suspension 3 days after the last booster immunization.

Preparation of spleen cell suspension: the spleen was taken out under aseptic conditions, washed once with incomplete medium, passed through a syringe needle to break the tissue and then passed through a stainless steel mesh in a plate to obtain a cell suspension. Number of cells was counted. Generally, the spleen volume of the immunized mouse was about twice the spleen volume of normal mouse, and the number of cells was about $2 \times 10^8$.

4) Cell Fusion

The above obtained spleen cells and SP2/0 cells were fused together using PEG.

Process:

A. Logarithmically growing myeloma cells SP2/0 was centrifuged at 1000 rpm for 5 minutes, the supernatant was discarded. The cells were suspended with incomplete medium and then counted. The required number of cells was taken, washed twice with incomplete medium.

B. Immunized spleen cell suspension was prepared at the same time, washed twice with incomplete culture medium RPMI1640 without serum.

C. The myeloma cells and the spleen cells were mixed at a ratio of 1:5, and washed once with incomplete medium in a 50 ml plastic centrifuge tube, at 1200 rpm for 8 minutes.

D. The supernatant was discarded, and the residual liquid was removed so as not to affect the concentration of PEG.

E. The bottom of the centrifuge tube was hit gently to loosen the cell pellet slightly.

F. Fusion at room temperature:

G. Within 30 seconds, 1 ml of preheated 45% PEG (Merek, molecular weight 4000) containing 5% DMSO was added with stirring.

H. The mixture was incubated for 90 seconds.

I. Preheated incomplete medium was added to terminate the action of PEG: 1 ml, 2 ml, 3 ml, 4 ml, 5 ml and 10 ml PEG was added every 2 minutes.

J. The mixture was centrifuged at 800 rpm for 6 minutes.

K. The supernatant was discarded, and 6 ml of 20% fetal calf serum RPMI1640 was added to suspend the cells. Do not blow hard, so as not to spread the fused cells.

L. Complete medium was added according to the number of 96-well culture plates used, 10 ml for each 96-well plate.

M. The cell suspension after fusion was added to a 96-well plate containing feeder cells, 100 µl/well, and cultured at 37° C. in 5% $CO_2$ incubator.

(2) Hybridoma Selection Using HAT 24 hours after fusion, commercial reagent HAT (50× storage) selection medium was added. 1 ml HT and 1 ml HAT were added to 50 ml of complete medium containing 20% calf serum.

Since the feeder cells and the fused cells had been added to the culture plate, 200 µl/well. Therefore, 3 times the amount of HAT should be added to the culture solution.

50×HAT (hypoxanthine (H), aminopterin (A) and thymidine (T)), the concentrations are as follows respectively:

H: $5 \times 10^{-3}$ M

A: $2 \times 10^{-5}$ M

T: $8 \times 10^{-4}$ M

After adding HAT selection medium and maintaining the culture for two weeks, the HT medium was used instead, the culture was maintained for two weeks; and then the general culture solution was used instead.

The cells after fusion were evenly spread on ten 96-well plates, and after 7-12 days, the supernatant was aspirated and detected by ELISA. The antigen-positive clones were selected and transferred to a 24-well culture plate, and after 3 days, the specific binding ability of the antibody to the antigen in the supernatant was detected by ELISA and WB respectively. The fusion conditions are as shown in Table 2.

TABLE 2

Fusion Number: 266CT  
Number of Spleen Cells: Whole Spleen  
PEG Volume: 1 ml  
Mouse Number: MS1148  
Number of Tumor Cells: $3 \times 10^{-7}$ (2) Clone Screening (WB and ELISA for screening positive clone)

a. Screen multiple clones and sub-clones by ELISA, and results are as shown in Table 3 and FIG. 3.

TABLE 3

| Sample Name | OD Value |
|---|---|
| Subclone 1 of 266CT10.5 | 1.775 |
| Subclone 2 of 266CT10.5 | 1.629 |
| Subclone 3 of 266CT10.5 | 1.767 |
| Subclone 4 of 266CT10.5 | 1.779 |
| Subclone 5 of 266CT10.5 | 1.675 |
| Subclone 1 of 266CT15.3 | 1.585 |
| Subclone 2 of 266CT15.3 | 1.663 |
| Subclone 3 of 266CT15.3 | 1.518 |
| Subclone 4 of 266CT15.3 | 1.643 |
| Subclone 5 of 266CT15.3 | 1.572 |
| Negative Control | 0.05 |
| Positive Control | 0.971 |

Result: On Apr. 25, 2011, the antigen-positive clones 266CT10.5 and 266CT.15.3 were subjected to subcloning. The cell culture supernatant of single clone was determined by ELISA, and the positive clone standard was OD value >1.0. The obtained 266CT10.5.1-5 and 266CT15.3.1-5 were positive clones. The positive clones were cultured in 24-well culture plate, when the bottom of the well was filled by cells, cells in each well was frozen in one ampoule, more than $1 \times 10^6$ cells per ampoule. Cell cryopreservation solution: 50% fetal calf serum, 40% incomplete medium, 10% DMSO (dimethyl sulfoxide).

Figures 1, 2, 3:
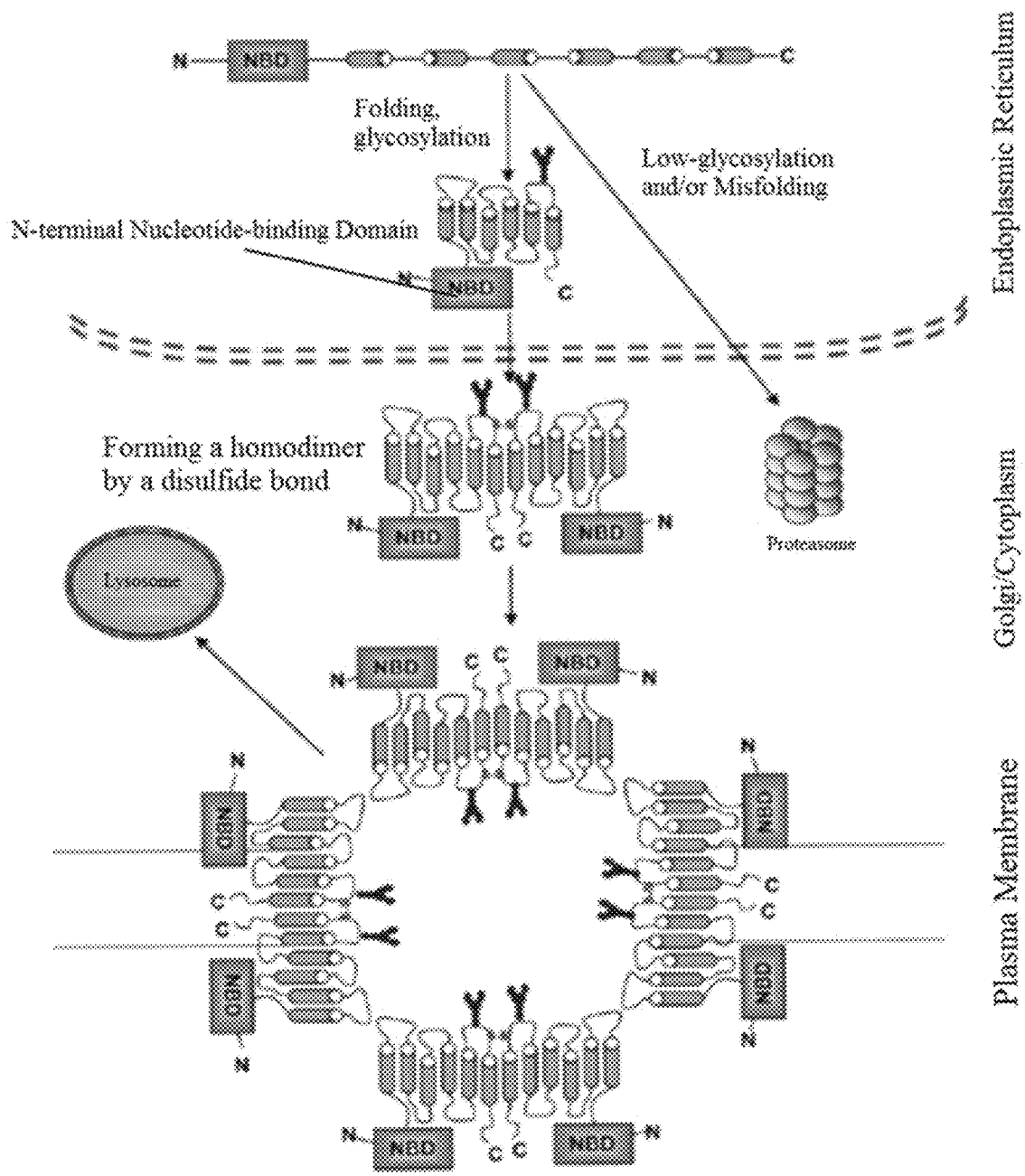
Figures 1, 2, 3, 4:
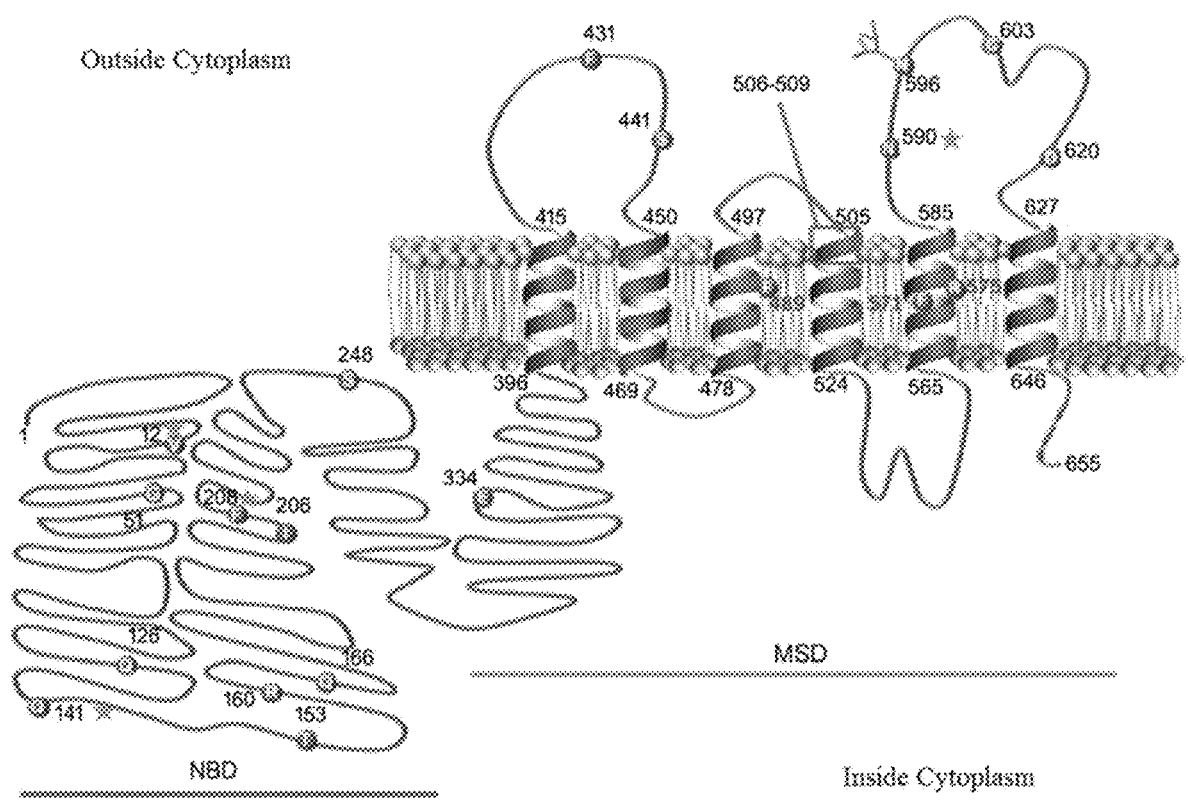

Ascites was detected by ELISA on May 11, 2011 and Mar. 20, 2013 to obtain clones 266CT10.5.1 and 266CT10.5.4, the specific results are shown in Table 4 and FIG. 4.

TABLE 4-1

| Date 2011 May 13 Clone Number 266CT10.5.1 Ascites Detection | | | | | | |
|---|---|---|---|---|---|---|
| Dilution Rate | 1/500 | 1/1000 | 1/2000 | 1/4000 | 1/8000 | 1/16000 |
| OD Value | 3.079 | 2.636 | 2.784 | 2.432 | 1.572 | 0.878 |
| Dilution Rate | 1/32000 | 1/64000 | 1/128000 | 1/256000 | 1/512000 | |
| OD Value | 0.568 | 0.329 | 0.196 | 0.143 | 0.109 | |

TABLE 4-2

| Date 2013 May 13 Colon Number 266CT10.5.4 Ascites Detection | | | | | |
|---|---|---|---|---|---|
| Dilution Rate | 1/500 | 1/1000 | 1/2000 | 1/4000 | 1/8000 | 1/16000 |
| OD Value | 3.492 | 3.165 | 2.948 | 2.664 | 1.882 | 0.988 |
| Dilution Rate | 1/32000 | 1/64000 | 1/128000 | 1/256000 | 1/512000 |
| OD Value | 0.746 | 0.594 | 0.344 | 0.283 | 0.188 |

The results shows that when the antibodies produced by hybridoma cells of clones 266CT10.5.1 (Table 4-1) and 266CT10.5.4 (Table 4-2) were double-diluted from 1:500, at a titer of 1:8000, both still had an OD>1.0. After obtaining the hybridoma clone, the cells were deposited, of which the deposit dates are Jun. 16, 2016 and Sep. 5, 2017, the address of deposit is No. 1 Beichen West Road, Chaoyang District, Beijing, China, and accession numbers are CGMCC12653 and CGMCC14683.

Example 2: Identification of Antibody Subtype

Antibody Subtype was identified by ELISA on May 13, 2011.

The mouse monoclonal antibody subtype identification kit (Proteintech, USA) was stored at 4° C., three ELISA strips were taken, the remaining stripes were put back in the sealed bag. The culture supernatant of the clone 266CT10.5.1 hybridoma cells was diluted with PBST (1:100), added to the sample well of the first stripe, 50 μl/well; the second stripe was set a negative control, only the same concentration of BSA was added, 50 μl/well; and positive antibody was added to the third stripe, 50 μl/well. No incubation was needed. 1× goat anti-mouse IgM+IgG-HRP was added to the sample wells, 50 μl/well. The stripes were mixed gently on a mixer for 1 minute, covered with plate-sealing films, incubated at room temperature for 1 hour. The liquid in the well was discarded, and the plate was washed 3 times with 1×PBST, patted dry with paper. Fresh prepared color solution was added to the well, 100 μl/well (color solution formula, solution A:solution B=1:100, i.e., 10 μl of A solution and 1 ml of B solution were mixed, used immediately after mixing). The color was developed at room temperature for 20 minutes in the dark, and 100 μl/well of stop solution was added. The result was determined by a microplate reader for OD value of OD 450 and the one with the highest value was IgG1 subtype.

TABLE 5

Subtype Identification Result

| Subtype | OD Value of Clone Number 266CT10.5.1 | OD Value of the Negative Control | OD Value of the Positive Control |
|---|---|---|---|
| IgG1 | 1.12 | 0.076 | 1.649 |
| IgG2a | 0.25 | 0.053 | 1.64 |
| IgG2b | 0.051 | 0.067 | 0.79 |
| IgG3 | 0.095 | 0.074 | 1.415 |
| IgM | 0.096 | 0.121 | 1.479 |
| IgA | 0.051 | 0.051 | 1.294 |
| Igk | 0.696 | 0.048 | 1.156 |
| Igλ | 0.051 | 0.055 | 0.737 |

Note:
Negative antibody—the sample that did not contain the test subtype, positive antibody—the sample containing the test subtype.

Using the positive clone as a reference, the clone only showed an OD value >1 when measuring the IgG1 subtype, which was 1.12, so the subtype of this clone was finally identified as IgG1. The hybridoma cell supernatants of clones 266CT10.5.4 (under accession number CGMCC14683) and 266CT15.3.2 (under accession number CGMCC14684) were determined using the same method, and the subtype of both was IgG1.

Example 3: Obtaining of Monoclonal Antibody

1. Hybridoma Cell Resuscitation and Culture Expansion
    1) Cell culture medium was added to a 12-well cell culture plate, about 2 ml per well.
    2) The cryopreserved cells under accession number of CGMCC12653 were taken out from the liquid nitrogen tank and rapidly thawed in a 37° C. water bath.
    3) The thawed cells were transferred into 5 ml of cell culture medium, and then transferred to a centrifuge tube, centrifuged at 800 rpm for 8 minutes.
    4) The supernatant in the centrifuge tube was aspirated, and 3 ml of the cell culture medium was added to mix the precipitated cells. The cells were put into the corresponding culture plate wells at 1 ml/well. The cell number, cell morphology, impurity and whether there was contamination in the background were observed under a microscope. The plate was placed in an incubator for incubation.

The hybridoma cells of clone number 266CT10.5.4 and clone number 266CT15.3.2 were resuscitated and expanded using the same method.

2. Collect and Inject Hybridoma Cells
    1) The logarithmically growing cells cultured as above were collected. 1 ml of the supernatant was aspirated and then the cells were blown and detached from the culture surface. The cells were collected into a 15 ml centrifuge tube, and centrifuged at 800 rpm for 8 minutes.
    2) The supernatant after the centrifugation was aspirated and 4 ml of physiological saline was added to the tube. After the cells were suspended, the cells were centrifuged again under the same condition, the supernatant was discarded, and then 2 to 3 ml of physiological saline was added to the tube. The cells were suspended, transferred into a 5 ml syringe and injected into the abdominal cavity of the mice (the mice were intraperitoneally injected with liquid paraffin 1 week before) at 1 ml to 0.5 ml/mouse. One week later, the abdominal cavity uplift of the mice and the activities of the mice were observed daily to prevent the mice from dying.

The hybridoma cells of clones 266CT10.5.4 and 266CT15.3.2 were collected and intraperitoneally injected using the same method.

3. Collect Ascites

Mice with abdominal uplift and had been immunized as the above were sacrificed, immersed in alcohol for disinfection. The abdomen epithelium was cut with scissors, the abdominal skin was torn open, the peritoneum was lifted up and cut open, a straw was inserted, the ascites was squeezed, and the ascites was aspirated into a 15 ml centrifuge tube, centrifuged at 800 rpm for 30 minutes. A pale yellow liquid under the lipid layer was collected, which was the ascites containing antibody.

2) Under normal circumstances, 2 to 3 ml of ascites was collected from each mouse. The antibody concentration was 0.5 to 5 mg/ml. The ascites was aliquoted in 1.5 ml EP tube, 1 ml/tube, and then stored at −80° C.

4. Antibody Purification

1) Protein G affinity chromatography column preparation: 1 ml of filler was loaded into a column; ethanol was washed away using 3 to 5 bed volumes of ultrapure water; the column was equilibrated by 5 to 10 bed volumes equilibration buffer.

2) Loading: first, the ascites sample obtained in the foregoing (6) was subjected to ultrafiltration concentration to 1 ml, and then it was loaded to the column.

3) Washing: the column was washed with 5 to 10 bed volumes of equilibration buffer until no significant color reaction was observed when the flow-through liquid was tested with detection solution.

4) Elution: target antibody adsorbed on the filler was eluted using elution buffer, the eluent (1-6 tubes) was collected and immediately neutralized to neutral condition with neutralizing buffer. The monoclonal antibody of interest was obtained.

Note: the ascites antibody produced by the hybridoma cell of clone number 266CT10.5.1 in Example 2 (CG-MCC12653) was named ABCG2-PKU1, the ascites antibody produced by the 266CT10.5.4 hybridoma cells in Example 1 was named ABCG2-PKU1-1, the ascites antibody produced by the clone number 266CT15.3.2 hybridoma cells was named ABCG2-PKU2.

Example 4: Preparation of Drug-Resistant Cell Lines

1. MCF7/ADM and A549/cis cells were purchased from Cancer Hospital, Chinese Academy of Medical Sciences (MCF7/ADM is breast cancer cell line MCF7 resistant to adriamycin, A549/cis is lung cancer cell line resistant to cisplatin).

2. Induction of MCF7/FLV2000 and SW480/MX2500 drug-resistant tumor cell lines (FLV: floripiridol; MX: mitoxantrone).

In the past experiments, the drug-resistant tumor cell lines were usually incubated with antitumor drugs at a low concentration, and then the concentration was gradually increased to a high concentration, which took 1-2 years to obtain a stable drug-resistant strain. The drug-resistant of the tumor cells induced by this method usually belong to the acquired resistance, which is quite different from the drug resistance developed by the cancer patients in clinic. Based on the reported literature (Wang X Q, Ongkeko W M, Chen L, Yang Z F, Lu P, Chen K K, Lopez J P, Poon R T, Fan S T. Octamer 4(Oct4) mediates chemotherapeutic drug resistance in Liver Cancer Cells through a Potential Oct4-AKT-ATP-binding Cassette G2 Pathway, Hepatology. 2010 August; 52(2):528-39. doi:10.1002/hep.23692), some improvements were made. We used an administration method which was acceptable and close to the clinical treatment for tumor patients. First, 50 nM of FLV was added to the dish in which breast cancer MCF7 cells were cultured. After the first administration, more than 95% of the cells underwent apoptosis, senescence and then died; the drug-resistant clones were screened, which showed high similarity to the tumor stem cell with a stable drug resistance gene ABCG2. After 5 passages, the administration was repeated 4-5 times, and the dose was increased by 2-2.5 times each time to 100 nM, 200 nM, 500 nM and 1000 nM. Less than 5% of drug-resistant cell clones were obtained, the cells were expanded to the $8^{th}$ generation and frozen for later use. Subsequently, the same administration method was used, colon cancer SW480 cells were treated with 100 nM mitoxantrone. After the first administration, more than 95% of the cells underwent apoptosis, senescence and then died; the drug-resistant clones were screened, which showed high similarity to the tumor stem cells with a stable drug resistance gene ABCG2. After 3 passages, the administration was repeated 4-5 times, and the dose was increased by 2-2.5 times each time to 200 nM, 500 nM and 1000 nM. Less than 5% of drug-resistant cell clones were obtained, the cells were to the $8^{th}$ generation and frozen for later use. Breast cancer MCF7 cell resistant to 2 μM FLU was named MCF7/FLV2000, and colon cancer SW480 cell resistant to 2.5 μM MX was named SW480/MX2500.

3. Identification of ABCG2 Expression in Drug-Resistant Tumor Cells MCF7/FLV2000 and SW480/MX2500

(1) mRNA Expression Level of Drug Resistance Gene

Total RNA extraction: total RNA from cells was extracted using QIAGEN's RNAeasy plus kit. All EP tubes and pipette tips used in the experiment were made from RNase-free material; the water was treated to inactivate RNase (0.1% DEPC was added, vigorously shaken to mix thoroughly, reacted at 37° C., and DEPC was removed the next day by autoclave). 1 ml of Trizol was added to the adherent cells in a Petri dish with a diameter of 3.5 cm; after repeated blowing and suction with the tip, cell lysate was transferred to an EP tube, allowed to stand at 4° C. for 5 minutes; 0.2 ml of chloroform was added, shaken vigorously for 15 seconds, allowed to stand at 4° C. for 5 minutes; the tube was centrifuged at $13 \times 10^3$ rpm at 4° C. for 15 minutes; the upper aqueous phase was transferred to a new tube, 0.5 ml of isopropanol was added, allowed to stand at 4° C. for 5 minutes; the tube was centrifuged at $13 \times 10^3$ rpm at 4° C. for 15 minutes to precipitate the RNA; the supernatant was discarded, 1 ml of 75% alcohol was added to wash the precipitation, the tube was centrifuged at $8 \times 10^3$ rpm at 4° C. for 5 minutes; the supernatant was discarded and the precipitation was dried for 10 minutes; an appropriate amount of DEPC-treated water was added to dissolve the RNA, and 1 μl of the RNA was diluted and the total RNA content was measured.

Synthesis of the first strand cDNA: Super-Script™ Pre-amplification System for First Strand cDNA Synthesis kit purchased from GIBICOL was used.

1) 2 μg of total RNA was added into a 0.5 ml microcentrifuge tube, an appropriate amount of DEPC-H$_2$O was added to make the total volume 11 μl. 1 μl of 10 μM Oligo (dT) was added to the tube, mixed gently, and centrifuged.

2) The microcentrifuge tube was heated at 70° C. for 10 min, and immediately inserted into an ice bath for at least 1 minute. Then a mixture of the following reagents was added:

| 10 × PCR Buffer | 2 μl |
|---|---|
| 25 mM MgCl$_2$ | 2 μl |
| 10 mM dNTP | 1 μl |
| 0.1M DTT | 2 μl |

The reagents were mixed gently, centrifuged and incubated at 42° C. for 5 minutes.

3) 1 μl of Superscript II was added, incubated in a 42° C. water bath for 50 minutes to obtain the cDNA.

Quantitative Real-Time PCR

The SYBR Green Real-time PCR Master Mix purchased from TOYONO was used for

PCR reaction system.

| 2 × SYBR Green Master Mix buffer | 7.5 µl |
| --- | --- |
| Forward Primer (10 pmol/µl) | 0.15 µl |
| Reverse Primer (10 pmol/µl) | 0.15 µl |
| Sterilized DEPC Water to | 6.2 µl |
| Mixing Tube Volume | 14 µl |

Note:
Each Sample Tube Volume = Mixing Tube Volume (14 µl) + cDNA Template (1 µl)

Internal control primer for the experiment: GAPDH

Primers for the experiment: drug resistance genes p-gp, MRP1 and ABCG2

The PCR reaction was carried out in ABI 7700 quantitative PCR machine.

PCR reaction conditions, first stage: 95° C. for 10 minutes; second stage: 95° C. for 15 seconds, 60° C. for 1 minute, 40 cycles; amplified mRNA was obtained.

3) Data analysis: The Ct value (Cycle threshold) of the sample was detected, and differences in expression of the specific genes between different samples were determined by calculating $2^{-\Delta\Delta Ct}$. To reduce the systematic error and sample error, triplicate wells were set for the samples GAPDH, p-gp, MRP1 and ABCG2. The average of the triplicate wells was used as the Ct value of the sample, and then $2^{-\Delta\Delta Ct}$ was calculated according to the following formula. The experiment was repeated at least three times and the result is shown in the histogram as mean±standard deviation.

Figures 1, 2, 3, 4, 5:
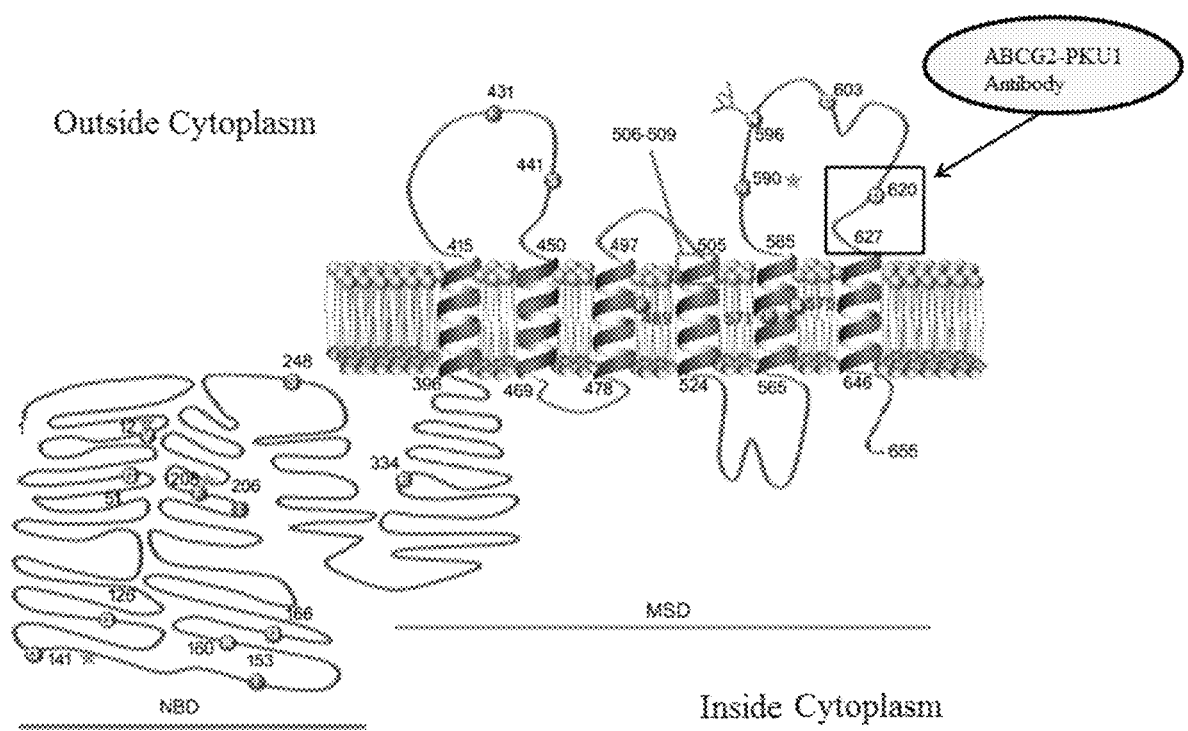
Figure 2:
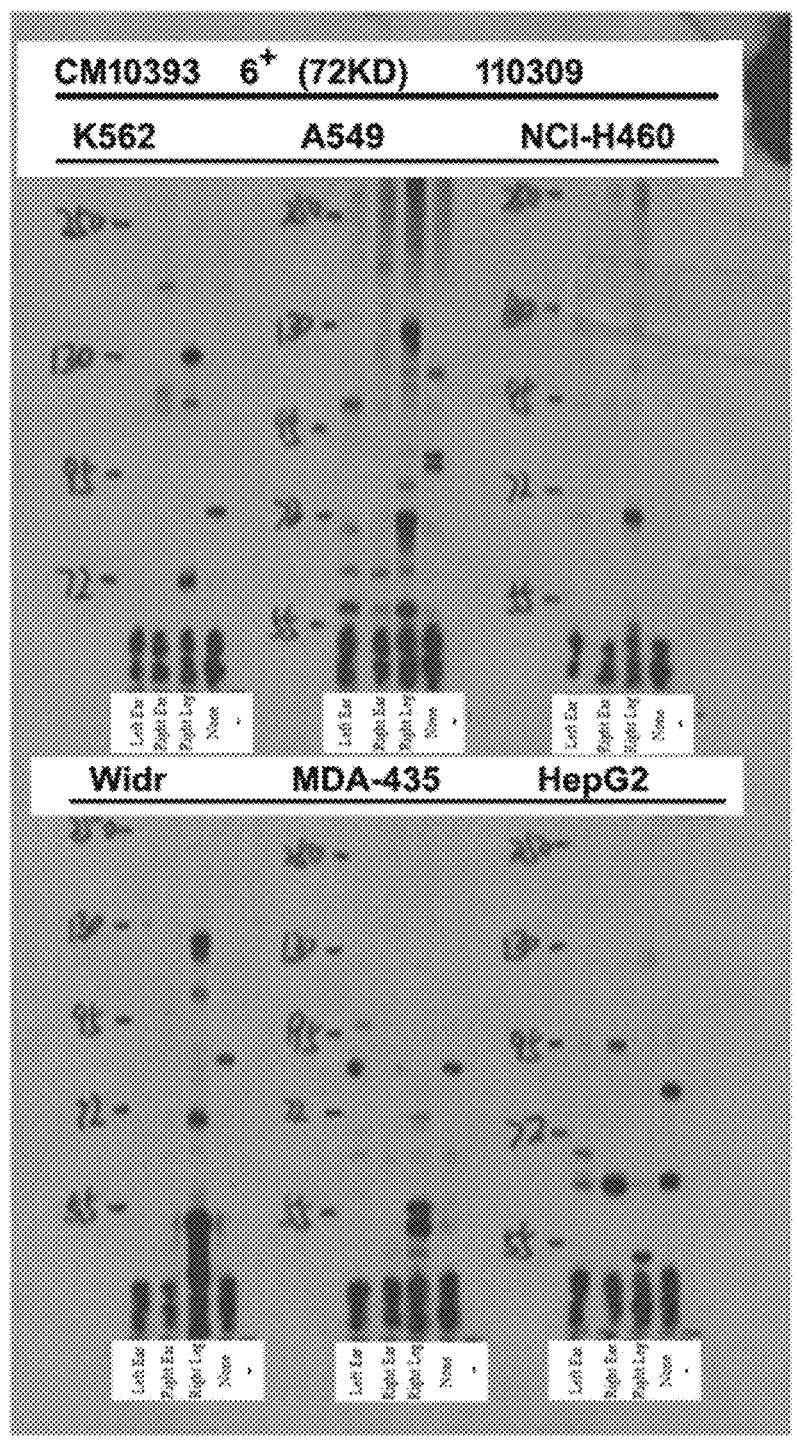
Figure 3:
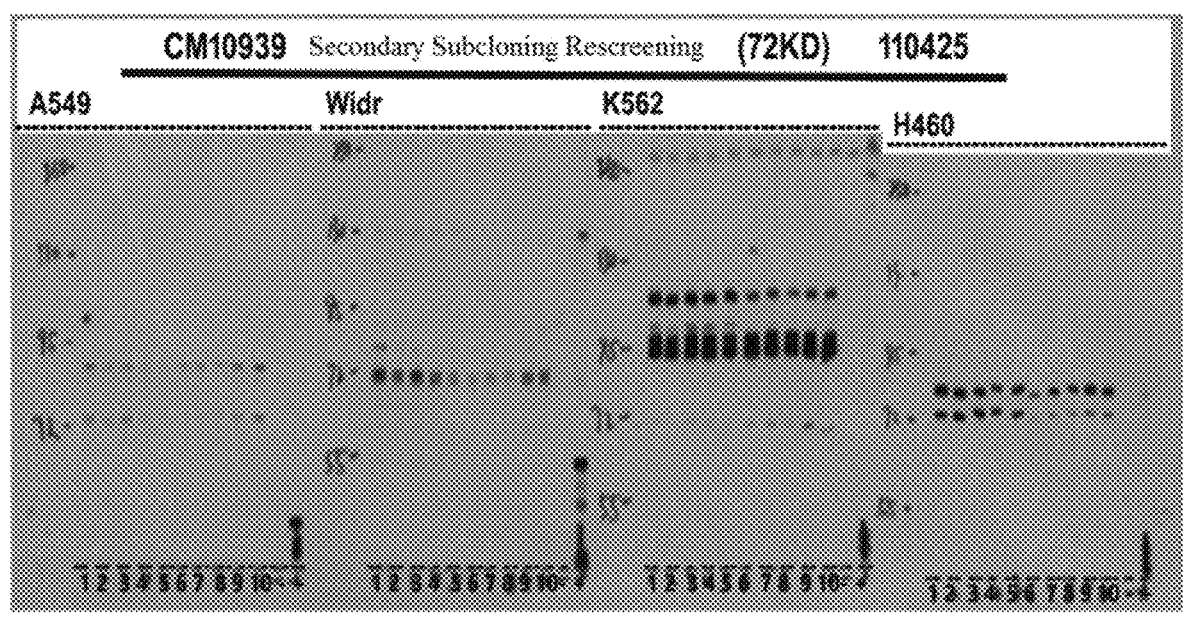
Figures 1, 4:
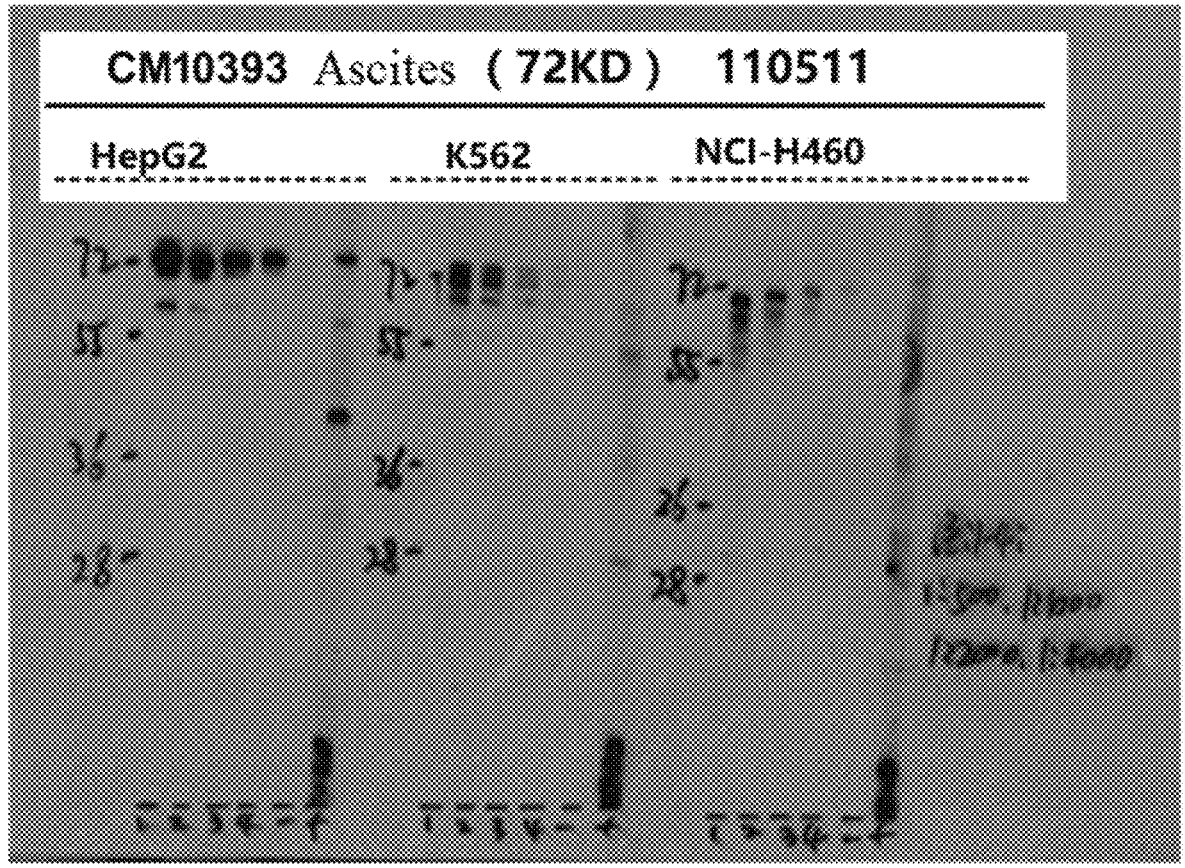
Figures 2, 4:
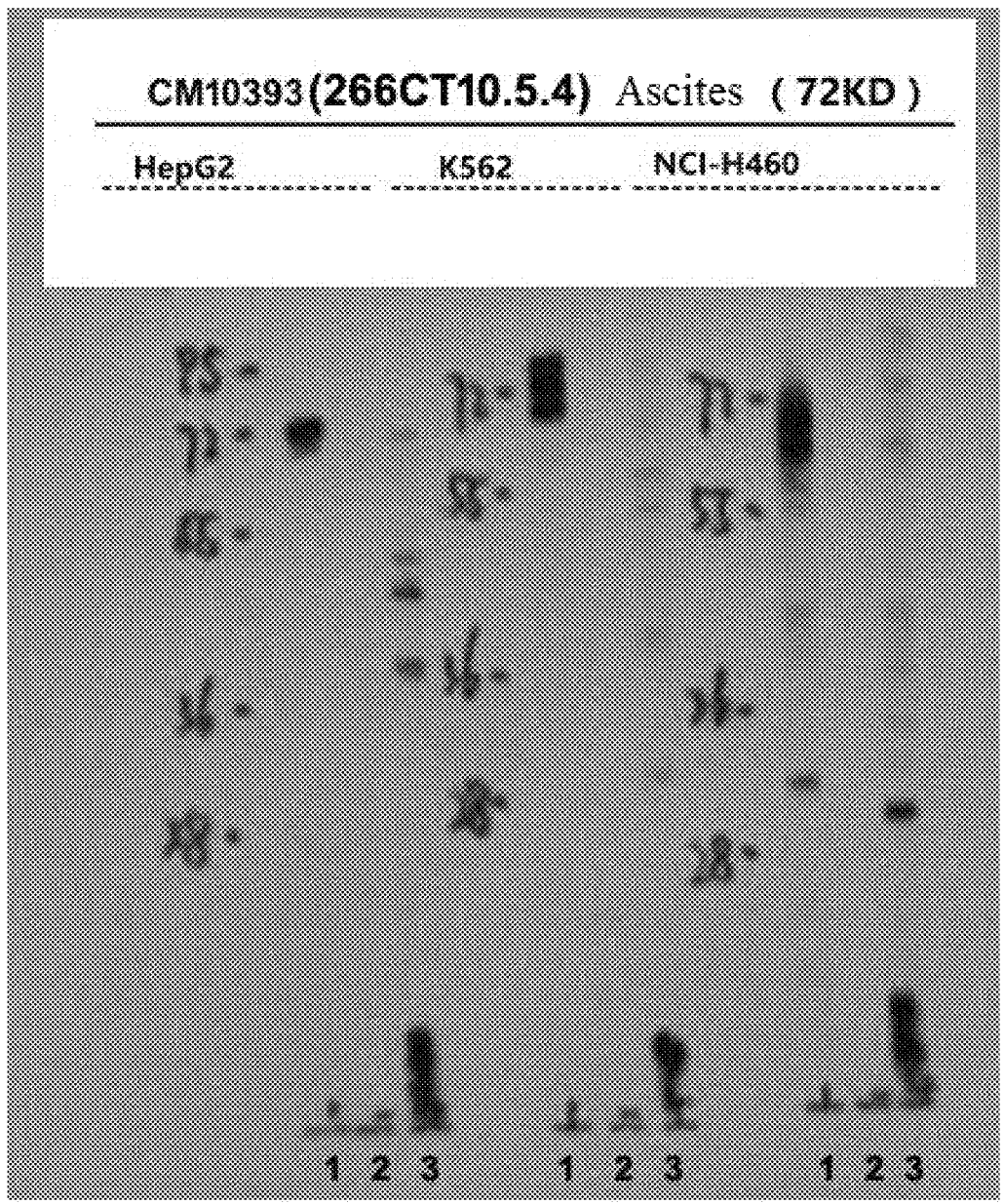
Figure 5:
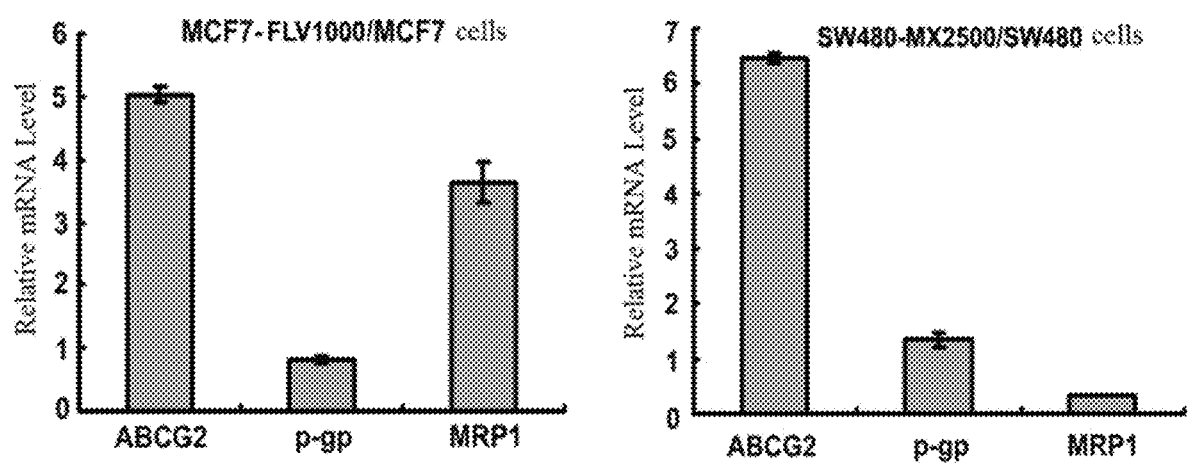

$\Delta$Ct experimental group=Ct experimental group gene−Ct experimental group internal control $\Delta$Ct control group=Ct control group gene−Ct control group internal control $\Delta\Delta$Ct=$\Delta$Ct experimental group−$\Delta$Ct control group $2^{-\Delta\Delta Ct}=2^{-(\Delta Ct\ experimental\ group-\Delta Ct\ control\ group)}$ The result is as shown in FIG. 5. The mRNA expression levels of all the test drug resistance genes in drug-resistant strains MCF7/FLV1000 and SW480/MX2500 were increased compared with breast cancer cell MCF7 and colon cancer cell SW480, particularly, the mRNA expression level of ABCG2 was increased by more than 5 times.

(2) Protein Expression Level of Drug Resistance Gene by Western Blot

Sample Preparation

1) MCF7, MCF7/FLV1000, SW480 and SW480/MX2500 cells in 100 mm diameter petri dishes were collected to 1.5 ml centrifuge tube, respectively, centrifuged at 10,000 g for 1 minute.

2) Lysis buffer RIRP (50 mM Tris (pH 7.4), 150 mM NaCl, 1% Triton X-100, 1% sodium deoxycholate, 0.1% SDS, and 2 mM sodium pyrophosphate, 25 mM β-glycerophosphate, 1 mM EDTA, 1 mM $Na_3VO_4$, 0.5 ug/ml of leupeptin and other protease inhibitors were added before use) was added, mixed well with a pipette.

3) The tube was centrifuged at 13000 g for 50 minutes, the supernatant was transferred to a new 1.5 ml centrifuge tube.

4) The protein content was determined by Lowrey method, and an equal volume of 2× loading buffer was added.

Western Blot

1) The separating gel and stacking gel were prepared separately to make a gel.

2) Protein denaturation: the protein samples prepared in step 4) of the first step was placed in boiling water for 10 minutes, and the pre-stained marker was boiled for 5 minutes at the same time.

3) Loading: 20-40 µl of sample was add to each well.

4) Electrophoresis: the gel was put in an electrophoresis tank under a constant current of 90 mA (2 plates) for 45-minute, if there was only one plate, the current was set to 50 mA.

5) The gel was taken out, and cut with a cutter.

6) The gel was placed in transfer buffer for immersion;

7) The following materials were placed in order: black piece→sponge→filter paper→gel→NC membrane→filter paper (bubbles were remove with a pipette)→sponge.

8) The structure prepared in 7) was placed in a membrane transfer tank in the right direction, ice cubes were added, and transfer buffer was added.

9) The electrodes were connected, and the transfer was carried out at a constant voltage of 100 V for 90 minutes.

10) The membrane was taken out and stained with Ponceau S.

11) Ponceau S was washed off with TBST.

12) Blocking: blocking buffer (5% non-fat milk powder+ TBST) was added and incubated in a shaker at room temperature for 1 hour.

13) The blocking buffer was recovered; primary antibody, mouse ABCG2 antibody diluted with 5% BSA+TBS, was added.

14) The membrane was put in a 4° C. shaker overnight.

15) The primary antibody was recovered, and the membrane was washed with TBST for 10 minutes, 3 times in total.

16) HRP-labeled rabbit anti-mouse secondary antibody (diluted with 5% nan-fat milk powder+TBS) was added, incubated in a shaker at room temperature for 1 hour.

17) The secondary antibody was recovered, and the membrane was washed with TBST for 10 minutes, 3 times in total.

18) The membrane was immersed in ECL luminescence solution for 1 minute.

19) The membrane was placed in a cassette, exposed in a dark room, and the film was washed.

Figure 6:
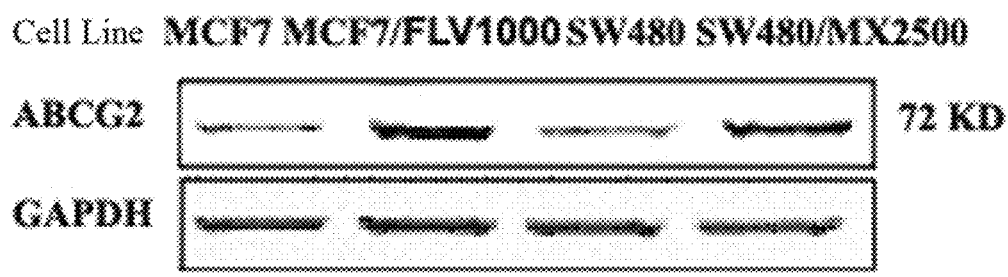
FIG. 6 shows Western blot detection of drug-resistant cells. The lanes were labeled as 1-4 from left to right: breast cancer cell MCF7 (lane 1) and its drug-resistant strain MCF7/FLV100 (lane 2), and colon cancer cell SW480 (lane 3) and its drug-resistant strain SW480/MX2500 (lane 4). The result shows that the protein expression levels of the drug resistance gene ABCG2 in the drug-resistant strains MCF7/FLV1000 and SW480/MX2500 (lanes 2 and 4) were 1-2 times higher than those of breast cancer cell MCF7 and colon cancer cell SW480 (lanes 1 and 3).

The result is as shown in FIG. 6. Western Blot showed that the protein expression levels of the drug resistance gene ABCG2 in the drug-resistant strains MCF7/FLV1000 and SW480/MX2500 (lanes 2 and 4) were 1-2 times higher than that in breast cancer cell MCF7 and colon cancer cell SW480 (lanes 1 and 3).

(3) Immunofluorescence Assay (Detect the Expression Level of Drug Resistance Proteins to Verify the Result of Western Blot)

Method:

1) MCF7, MCF7/FLV1000, SW480 and SW480/MX2500 cells were seeded onto a coverslip at an appropriate density one day before the experiment, and incubated at 37° C.

2) The medium was removed, and the cells were washed 3 times with PBS.

3) The cells were fixed with 4% paraformaldehyde (0.1 M PBS/pH 7.4) for 15-30 minutes.

4) The cells were washed 3 times with PBS.

5) 2% BSA (PBS/pH 7.4) was added, and the coverslips were blocked at 37° C. for 30 minutes.

6) Primary antibodies was added, i.e. the three ABCG2 antibodies obtained in Example 3, which were respectively ABCG2-PKU1, ABCG2-PKU1-1 and ABCG2-PKU2, and commercial ABCG2 (BXP-21), p-gp and MRP1 antibodies (primary antibody was diluted with 2% BSA; IgG antibody, ABCG2 antibody and MPRI antibody were diluted at 1:100, P-gp antibody was diluted at 1:200), incubated at room temperature in a wet box overnight.

7) The coverslips were washed 3 times with PBS on the next day.

8) Secondary antibody (rabbit anti-mouse Dyelight 594) was added at a dilution rate of 1:100, incubated at room temperature in a wet box for 1 hour.

9) The coverslips were washed 3 times with PBS, and then 1 μl of DAPI was added to stain the nucleus.

10) About 10 μl of mounting medium was added dropwise to a slide, the stained coverslip was reversely attached to the slide. The slide was observed under a confocal microscope, and the images were collected and analyzed.

Figure 7:
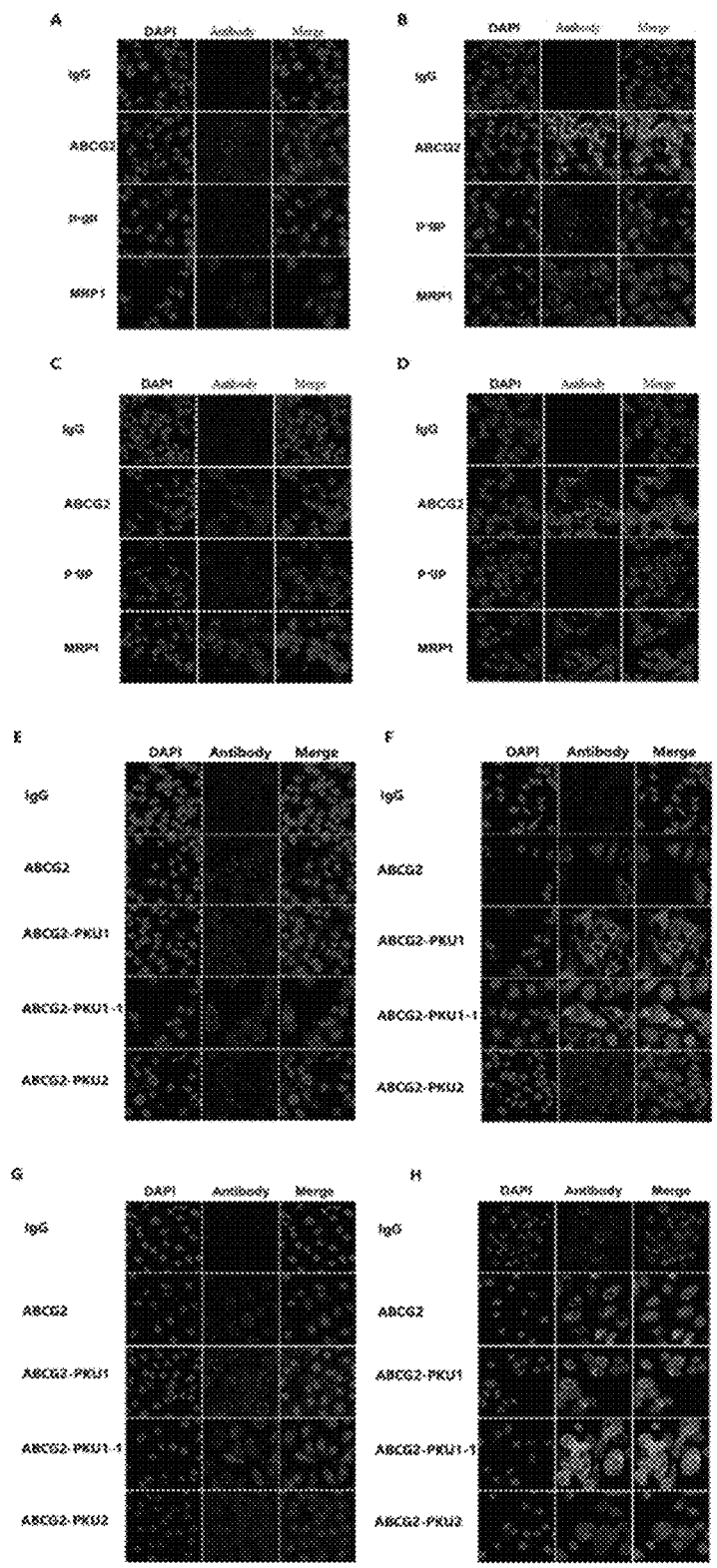
FIG. 7 shows immunofluorescence staining. A and E are breast cancer cell MCF7, B and F are drug-resistant strain MCF7/FLV1000, C and G are colon cancer cell SW480, D and H are drug-resistant strain SW480/MX2500. The left images are DAPI staining showing the nucleus (dark gray); the middle images show binding of IgG or antibodies against drug-resistant gene-expressing proteins through a secondary antibody (rabbit anti-mouse Dylight 594), which stained the cell membrane and cytoplasm (gray); while the right side are images of the overlapped photos of the staining on the left side and the middle. The result shows that comparing the drug-resistant strain MCF7/FLV1000 in Figure B with breast cancer MCF7 cells in Figure A, and comparing the drug-resistant strain SW480/MX2500 with colon cancer SW480 cells in Figure C, the staining signals of the middle and the right side were stronger with certain degrees compared to the control cells, wherein the protein expression level of ABCG2 was significantly enhanced, and p-gp and MRP1 were also increased to some extent. Comparing the drug-resistant strain MCF7/FLV1000 in Figure F with breast cancer MCF7 cell in Figure E, and comparing the drug-resistant strain SW480/MX2500 in Figure H with colon cancer SW480 cell in Figure G, commercial antibody (BXP-21), as the positive control antibody of ABCG2, shows the same staining intensity as the antibody ABCG2-PKU2. The staining signal of the antibody ABCG2-PKU1-1 was significantly stronger than that of the antibody ABCG2-PKU1, and the staining signal of the antibody ABCG2-PKU2 was the weakest.

The result is as shown in FIG. 7. FIGS. 7A and B show that, compared with breast cancer cell MCF7 and colon cancer cell SW480, the protein expression levels of the drug resistance gene ABCG2 in the drug-resistant strains MCF7/FLV1000 and SW480/MX2500 indicated by the immunofluorescence signal were significantly stronger; the expressions of p-gp and MRP1 were also increased in certain degrees. FIGS. 7C and D show that the staining of the antibody ABCG2-PKU1-1 was the strongest, the antibody ABCG2-PKU1 ranked second, the antibody ABCG2-PKU2 and the commercial ABCG2 antibody (BXP-21) were relatively weak.

Example 5: Identification Biological Function of ABCG2 Purified Antibody In Vitro at Cellular Level Antibodies used in this example: ascites antibody named ABCG2-PKU1 in Example 3, produced by clone 266CT10.5.1 hybridoma cells with accession number CGMCC12653; ascites antibody named ABCG2-PKU1-1 in Example 1, produced by clone 266CT10.5.4 hybridoma cells with accession number CGMCC14683; and ascites antibody named ABCG2-PKU2 in Example 1, produced by clone 266CT15.3.2 hybridoma cells with accession number CGMCC14684.

1. Tumor Cell Growth Inhibition Analysis

Method:

(1) Tumor cell MCF7 and the drug-resistant strains MCF7/ADM, MCF7/FLV1000, MCF7/Mitoxantrone obtained and identified in Example 4, A549 and A549/cis, L02 and L02/Oct4 cells were seeded in a 96-well plate, 3000 cells/90 μl/well, 6 replicate wells, incubated at 37° C. overnight.

(2) According to the following Tables 6-1 and 6-2, mitoxantrone, commercial ABCG2 antibody (BXP-21) and the three ABCG2 antibodies ABCG2-PKU1, ABCG2-PKU1-1 and ABCG2-PKU2 obtained in Example 3 were added to the plate. The plate was then incubated in a, 5% CO2 incubator at 37° C. 10 μl of DMSO was added to the well at d1, d2, d3, d4, d5, and d6, and the absorbance was measured using an ELISA instrument after 2 hours.

(3) Inhibitory rate calculation: OD value of drug-treatment—blank OD value/OD value without drug-treatment—blank OD value, a growth inhibition curve was plotted.

Figure 8:
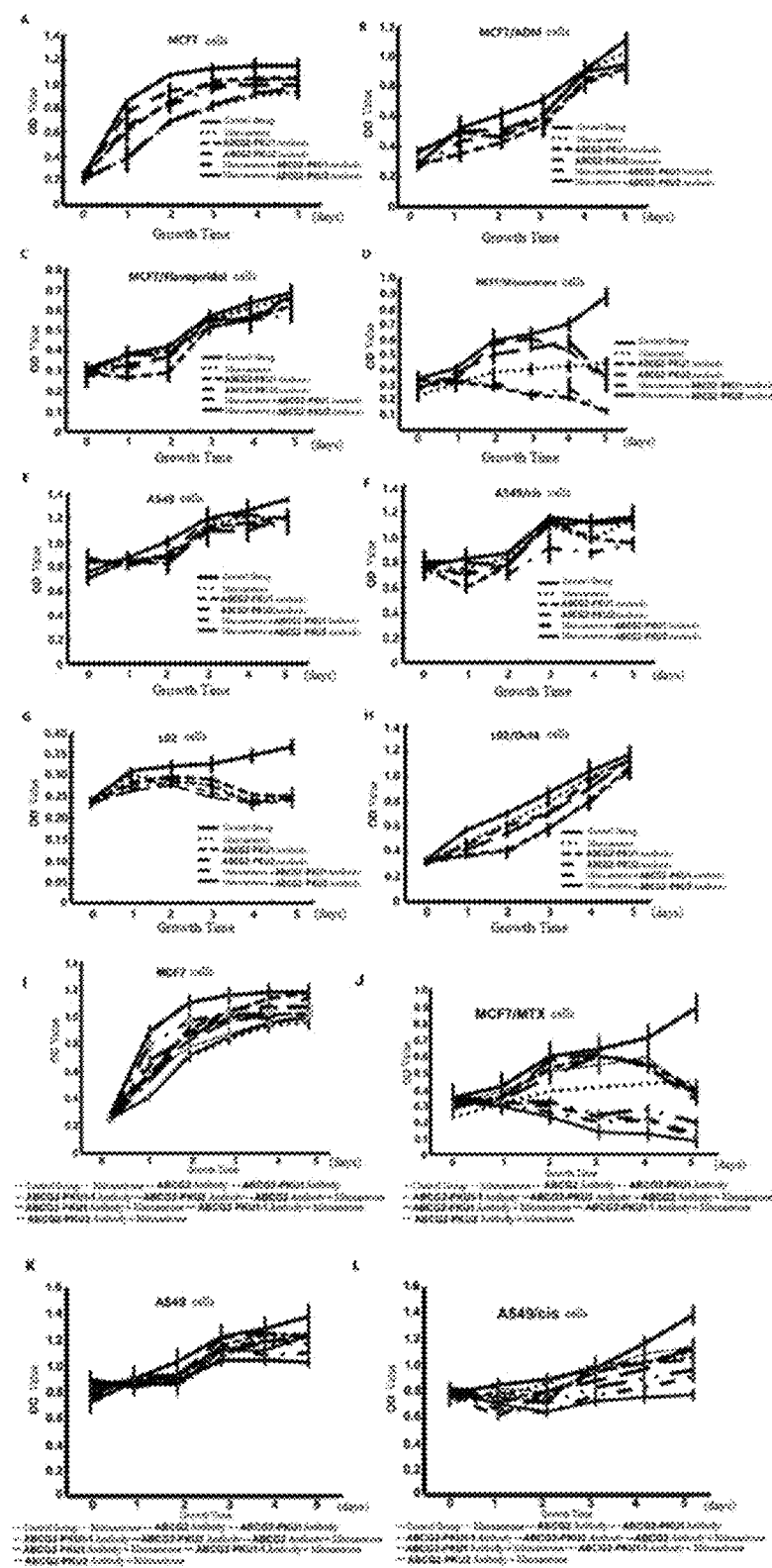
FIG. 8 shows growth inhibition analysis. A and I are breast cancer cell MCF7, B and J are drug-resistant strain MCF7/ADM, C is drug-resistant strain MCF7/Flavopiridol, D is drug-resistant strain MCF7/Mitoxantrone, E and K are lung cancer cell A549, F and L are drug-resistant strain A549/cis, G is hepatocytes L02, and H is L02/Oct4 cell line stably transfected with transcription factor Oct4.

The result is as shown in FIG. 8. Groups of mitoxantrone, ABCG2 antibody BXP-21, ABCG2-PKU1 antibody, ABCG2-PKU1-1 antibody and ABCG2-PKU2 antibody could inhibit the growth of tumor cells MCF7, A549 and the drug-resistant strains MCF7/ADM, MCF7/Flavopridiol, MCF7/Mitoxantrone, A549/cis and hepatic cells L02 and L02 transfected with Oct4. The ABCG2 antibody BXP-21, ABCG2-PKU1 antibody, ABCG2-PKU1-1 antibody and ABCG2-PKU2 antibody had the effect on enhancing the sensitivity of mitoxantrone, in particular, the effect of ABCG2-PKU1-1 antibody on enhancing the sensitivity of mitoxantrone was more obvious in ABCG2 high-expression MCF7/Mitoxantrone drug-resistant cells, the enhancement was more than one time better than that of the control antibody.

TABLE 6-1

| Tumor Cell | | | | | |
| --- | --- | --- | --- | --- | --- |
| Control | Mitoxantrone | ABCG2-PKU1 | ABCG2-PKU2 | ABCG2-PKU1 + Mitoxantrone | ABCG2-PKU2 + Mitoxantrone |

| Corresponding Drug-Resistant Strain | | | | | |
| --- | --- | --- | --- | --- | --- |
| Control | Mitoxantrone | ABCG2-PKU1 | ABCG2-PKU2 | ABCG2-PKU1 + Mitoxantrone | ABCG2-PKU2 + Mitoxantrone |

TABLE 6-2

| Tumor Cell | | | | | | | | | |
| --- | --- | --- | --- | --- | --- | --- | --- | --- | --- |
| Control | Mitoxantrone | ABCG2 Antibody | ABCG2-PKU1 | ABCG2-PKU1-1 | ABCG2-PKU2 | ABCG2 + Mitoxantrone | ABCG2-PKU1 + Mitoxantrone | ABCG2-PKU1-1 + Mitoxantrone | ABCG2-PKU2 + Mitoxantrone |

| Corresponding Drug-Resistant Strain | | | | | | | | | |
| --- | --- | --- | --- | --- | --- | --- | --- | --- | --- |
| Control | Mitoxantrone | ABCG2 Antibody | ABCG2-PKU1 | ABCG2-PKU1-1 | ABCG2-PKU2 | ABCG2 + Mitoxantrone | ABCG2-PKU1 + Mitoxantrone | ABCG2-PKU1-1 + Mitoxantrone | ABCG2-PKU2 + Mitoxantrone |

2. Cytometric Analysis of Drug Accumulation Experiment

1) Cells MCF7 and MCF7/ADM, A549 and A549/cis used for the experiment were collected.

2) The cells were washed three times with PBS by centrifuging at 1×10³ rpm for 5 minutes.

3) The cells were mixed well, and each type of the cells was equally divided into three centrifuge tubes, labeled as "1", "2" and "3"; "1" was a negative control, no antibody was added; "2" was a control group; and "3" was an experimental group, in which the antibodies ABCG2-PKU1, ABCG2-PKU1-1 and ABCG2-PKU2 prepared in Example 3 were added respectively (the amount of antibody was proportional to the cell density).

4) The tubes were incubated in a 37° C. incubator for 1 hour.

5) Mitoxantrone (MTX) was added to experimental group Tube "3", and mixed well.

6) The tubes were incubated in a 37° C. incubator for 1 hour.

7) After cells of the experimental group and the control group were thoroughly mixed, all cells were transferred to a test tube, placed on ice and then detected by a flow cytometer.

Figures 1, 9:
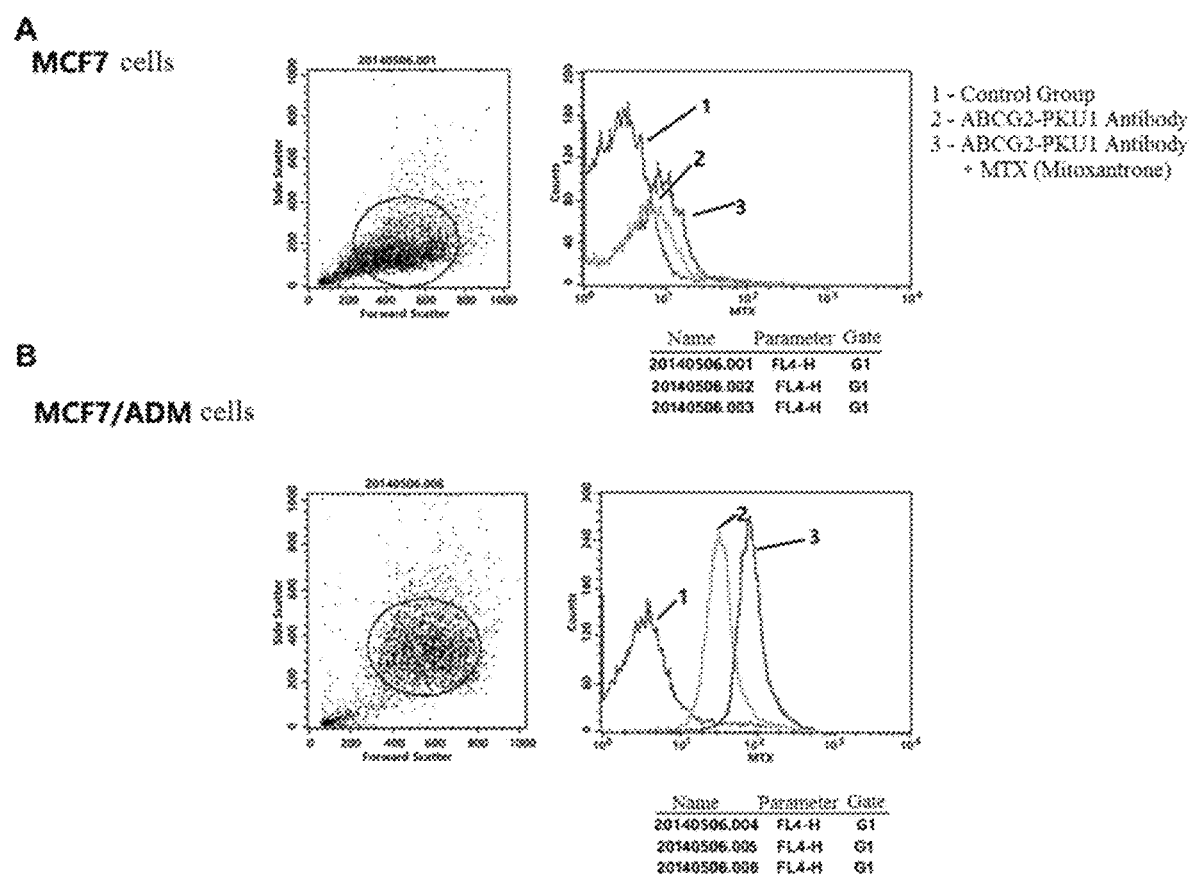
FIG. 9 shows the accumulation of mitoxantrone (MTX) in cells by flow cytometric analysis.
Figures 2, 9:
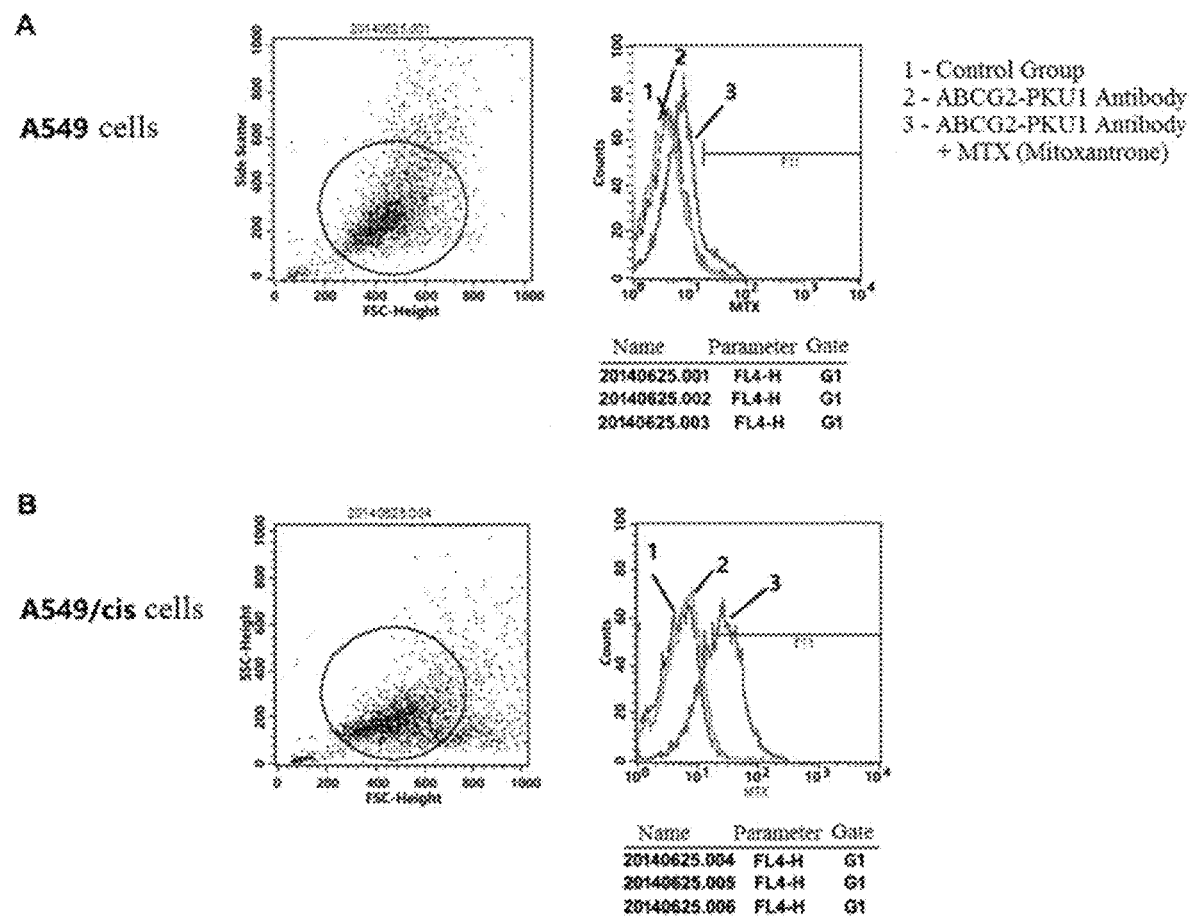
Figures 3, 9:
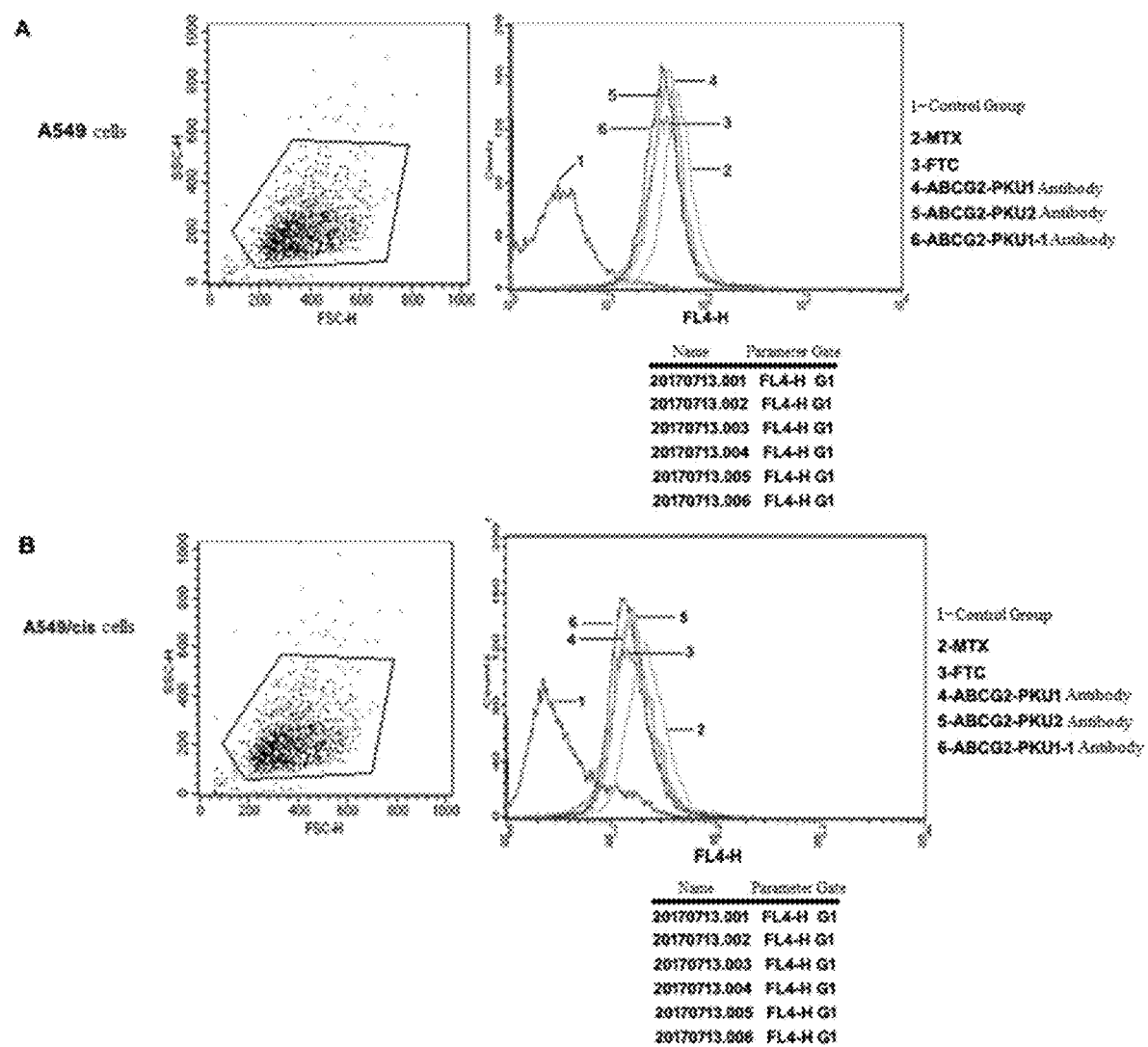

The result is as shown in FIG. 9. The accumulation of mitoxantrone (MTX) in cells was measured by flow cytometric analysis. In FIG. 9-1, A is breast cancer MCF7 cells, B is doxorubicin (ADM)-resistant strain MCF7/ADM; in FIG. 9-1, A is lung cancer A549 cells, B is cisplatin (CIS)-resistant strain A549/CIS. Wherein Curve-1 is the group of the cells without drug treatment, Curve-2 is the group of cells treated with the ABCG2-PKU1 antibody, and Curve-3 is the group of cells treated with the ABCG2-PKU1 antibody+MTX. The result shows that ABCG2 antibody could increase the accumulation of MTX in drug-resistant cells (Curve-3). FIG. 9-3 is the comparison of effects of antibodies ABCG2-PKU1, ABCG2-PKU1-1 and ABCG2-PKU2 on the accumulation of mitoxantrone (MTX) in tumor cells, wherein Curve-1 is group of the cells without drug treatment, Curve-2 is the group of cells treated with MTX, Curve-3 is the group of cells treated with the ABCG2 inhibitor FTC+MTX, Curve-4 is the group of cells treated with ABCG2-PKU1 antibody+MTX, Curve-5 is the group of cells treated with ABCG2-PKU1-1 antibody+MTX, Curve-6 is the group of cells treated with ABCG2-PKU2 antibody+MTX. The result shows that the effect of ABCG2-PKU1-1 antibody (Curve-5) on increasing the accumulation of MTX in tumor drug-resistant cells was slightly stronger than that of ABCG2 inhibitor FTC (Curve-3), the effect of ABCG2-PKU1 antibody (Curve-4) ranked second, and the effect of ABCG2-PKU2 antibody (Curve-6) was the weakest. This indicated that these three ABCG2-PKU monoclonal antibodies could reduce the efflux of ABCG2 substrate MTX in tumor drug-resistant cells MCF7/FLV1000 and A549/cis.

3. Drug Sensitization Test

MCF7 Flavo-resistant strain and A549 cisplatin-resistant strain (A549/cis) were used as the experimental cell line with high ABCG2 expression, and the corresponding non-resistant cells MCF7 and A549 with relatively low ABCG2 expression were used as control cell lines in the drug sensitization test. FTC is a specific inhibitor of ABCG2, so the cell group added with FTC was used as a positive control group; the cell group added with a corresponding volume of DMEM high glucose medium or RPMI-1640 medium was used as a negative control group. The selected antitumor drug was mitoxantrone (MTX), which is an active substrate of ABCG2.

The ABCG2-PKU1, ABCG2-PKU1-1 and ABCG2-PKU2 antibodies prepared in Example 3, as well as mitoxantrone (MTX) and FTC were added. After 72 hours, MTT test was carried out and the absorbance was measured. IC50 of mitoxantrone after addition of FTC and different concentrations of antibody was calculated. The ratio of the IC50 of the drug-resistant cells to the IC50 of the original cells was calculated, which was the relative drug resistance.

TABLE 7

Sensitization Effect of ABCG2 Antibody on Anti-tumor Drug in Tumor and Drug-resistant Cell Line thereof

| | Relative Drug Resistance | | | |
|---|---|---|---|---|
| | MCF 7 | MCF 7/ Flavo (Over-expressing ABCG2) | A549 | A549/ cis (Over-expressing ABCG2) |
| Mitoxantrone | 1.00 | 1.00 | 1.00 | 1.00 |
| +FTC (5 μM) | 1.03 | 0.77 | 1.13 | 0.92 |
| +ABCG2-PKU2 Antibody (2 μM) | 1.04 | 0.62 | 1.12 | 1.16 |
| +ABCG2-PKU2 Antibody (5 μM) | 1.03 | 0.44 | 1.08 | 1.15 |
| +ABCG2-PKU1 Antibody (2 μM) | 1.00 | 0.28 | 0.91 | 0.65 |
| +ABCG2-PKU1 Antibody (5 μM) | 0.96 | 0.21 | 0.68 | 0.50 |
| +ABCG2-PKU1 Antibody (10 μM) | 0.74 | 0.19 | 0.47 | 0.37 |
| +ABCG2-PKU1-1 Antibody (2 μM) | 1.00 | 0.22 | 0.89 | 0.60 |
| +ABCG2-PKU1-1 Antibody (5 μM) | 0.92 | 0.12 | 0.62 | 0.28 |
| +ABCG2-PKU1-1 Antibody (10 μM) | 0.70 | 0.10 | 0.41 | 0.25 |

The result of the data is as shown in Table 7. Breast cancer cell MCF7 and Flavopiridol (Flavo)-resistant strain MCF7/Flavo cells, lung cancer A549 cells and cisplatin (Cis)-resistant strain A549/Cis cells were divided into 11 groups in the growth inhibition analysis: (1) no drug treatment group, (2) mitoxantrone treated group, (3) mitoxantrone+FTC (5 μM)-treated group, (4) mitoxantrone+ABCG2-PKU2 antibody (2 μM)-treated group, (5) mitoxantrone+ABCG2-PKU2 antibody (5 μM)-treated group, (6) mitoxantrone+ABCG2-PKU1 antibody (2 μM)-treated group, (7) mitoxantrone+ABCG2-PKU1 antibody (5 μM)-treated group, (8) mitoxantrone+ABCG2-PKU1 antibody (10 μM)-treated group, (9) mitoxantrone+ABCG2-PKU1-1 antibody (2 μM)-treated group, (10) mitoxantrone+ABCG2-PKU1-1 antibody (5 μM)-treated group, (11) mitoxantrone+ABCG2-PKU1-1 antibody (10 μM)-treated group. 10 μl of MTT was added at 70 hours after the addition of drug, incubated in a 37° C. incubator for 2 hours, and then the OD value was determined by a microplate reader. The value of (1) no drug treatment group was used as denominator, the value of each drug-treated group was used as numerator, the obtained value was the relative drug resistance. The result shows that, similar to ABCG2 inhibitor FTC, ABCG2-PKU1, ABCG2-PKU1-1 and ABCG2-PKU2 monoclonal antibodies showed effect on enhancing sensitivity of antitumor drug mitoxantrone in MCF/Flavo and A549/cis drug-resistant cells, but the effect of the antibody ABCG2-PKU1-1 was more than one time that of the antibody ABCG2-PKU1, the effect of the antibody ABCG2-PKU2 was the weakest.

4. Apoptosis Analysis (Kit from Donging was Used)

1) Lung cancer A549 cells and cisplatin-resistant A549/cis cells were respectively seeded in a 30 mm dish, 4 dishes per cell type.

2) A549 and A549/cis cells were treated with 0.8 μM of the three anti-ABCG2 antibodies ABCG2-PKU1, ABCG2-PKU1-1 and ABCG2-PKU2 prepared in Example 3 at 72 h, 48 h and 24 h, respectively.

3) The cells were digested with trypsin after 3 days, centrifuged at 1000 rpm for 5 minutes, and the collected cells were washed twice with PBS.

4) The cell concentration at each time point was respectively adjusted to 1×10⁶/ml with 1× binding buffer, 100 μl was taken and mixed with 5 μl of Annexin V and 5 μl of PI, incubated for 15 minutes in the dark.

5) 400 μl of 1× binding buffer was added to each tube, and the cell sample was measured with a flow cytometer within 1 hour.

Figure 11:
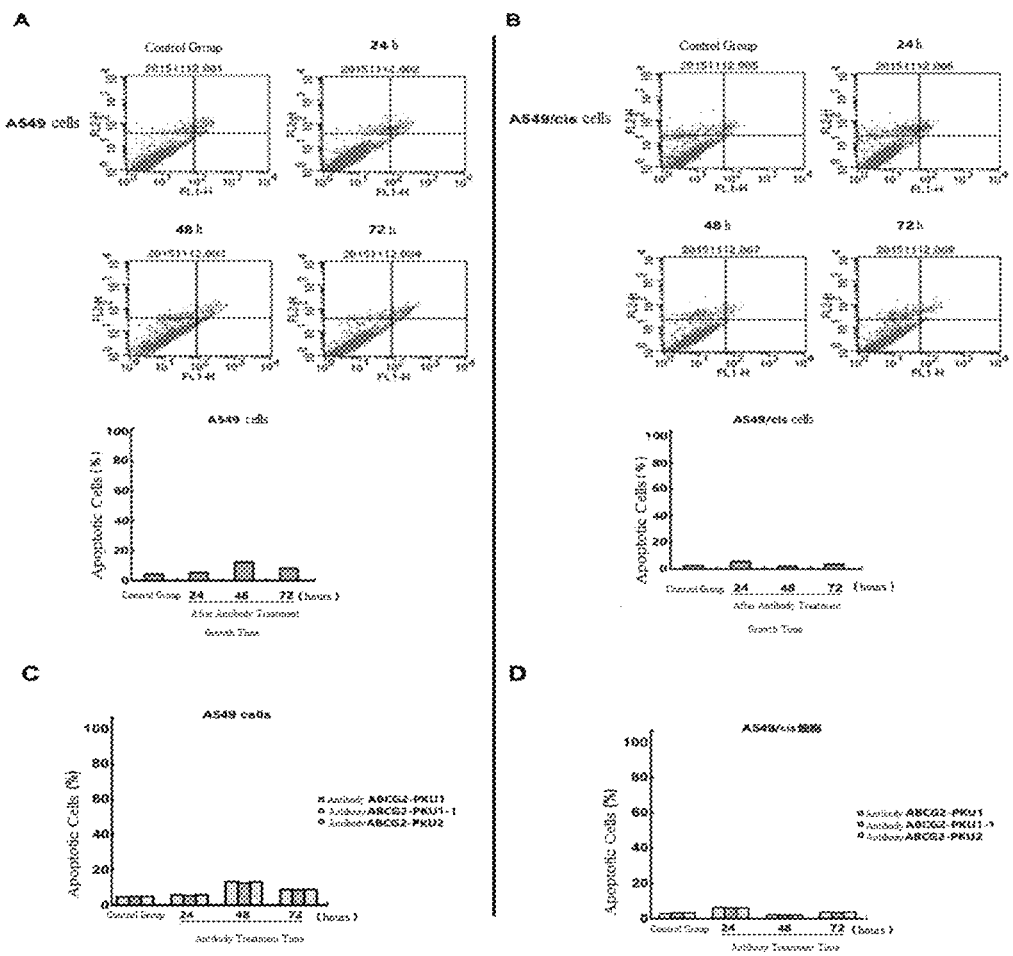
FIG. 11 shows apoptosis analysis.

The result of apoptosis analysis is as shown in FIG. 11. A and C represent lung cancer cell A549, B and D represent drug-resistant strain A549/cis. 0.8 μM of ABCG2-PKU1, ABCG2-PKU1-1 or ABCG2-PKU2 antibody was respectively added into a 30 mm Petri dish with lung cancer A549 cells or cisplatin-resistant strain A549/cis cells at 72 h, 48 h and 24 h. Cells were collected after 72 hours and tested. The result showed that within 72 hours of treatment, antibodies ABCG2-PKU1, ABCG2-PKU1-1 and ABCG2-PKU2 substantially did not cause apoptosis in lung cancer A549 cells and resistant strain A549/cis cells. The percentage of apoptotic cells was counted by histogram of the lower panel of FIGS. 11A and B as well as C and D. The result indicates that apoptosis is not the main mechanism by which ABCG2-PKU1, ABCG2-PKU1-1 and ABCG2-PKU2 antibodies act on tumor cells.

Conclusion: this experiment confirms that ABCG2-PKU1, ABCG2-PKU1-1 and ABCG2-PKU2 antibodies have the effect of reversing drug resistance of tumor cells by growth inhibition analysis, drug sensitization experiment, drug accumulation analysis and apoptosis analysis, and this effect is independent of the apoptosis of the cells.

Example 6: Identification Biological Function of ABCG2 Purified Antibody at Animal Level Female nude mice, 6-8 weeks, were randomly divided into non-administered group (control group), IgG group and ABCG2-PKU1 group, 5 per group. Lung cancer non-drug resistant cell A549 was inoculated in the left axilla, 5×10⁶/mouse. The formation of tumor was confirmed after three days. IgG and ABCG2-PKU1 antibodies were respectively injected into the mice via tail vein after one week, the dose was 0.3 mg/kg. The mice were weighed twice a week, and the drug was administered continuously for 3 weeks.

Figure 10:
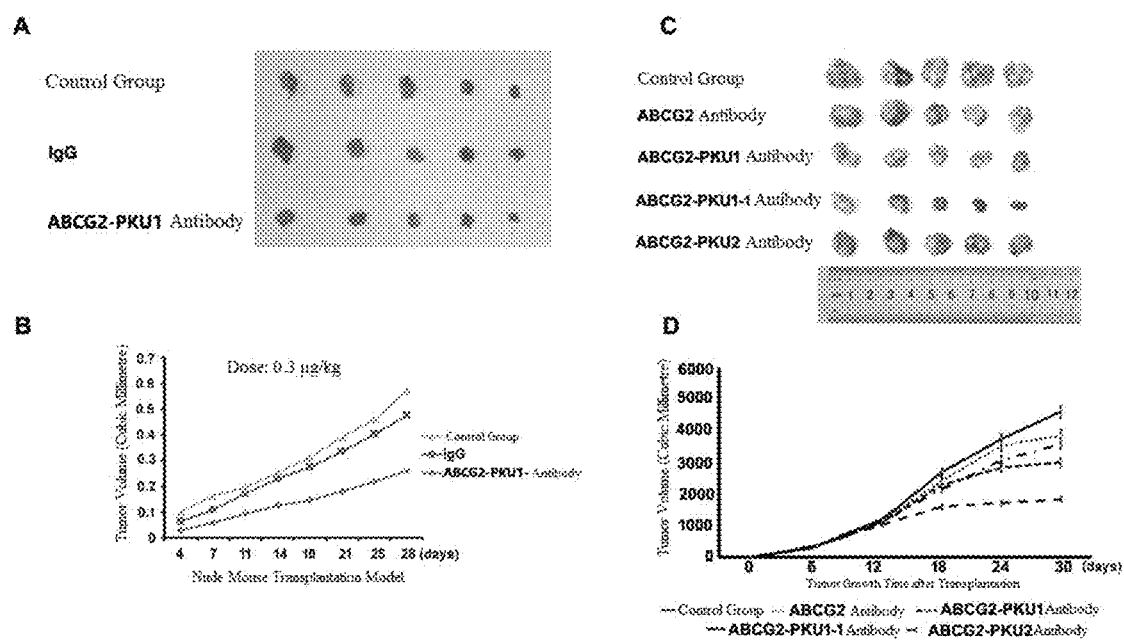
FIG. 10 shows the experiment of tumor formation in nude mice. Antibody ABCG2-PKU1 was administered after one week, once a week for three weeks. A control group, an IgG antibody-administrated group and an ABCG2-PKU1 antibody-administrated group were set in FIG. 10A, compared with the control group without administration and the IgG group, the ABCG2-PKU1 antibody group significantly reduced the size of the transplanted tumor. The nude mice in FIG. 10B were inoculated with $1 \times 10^7$ of lung tumor cells, and tumor volume was measured since the $4^{th}$ day of inoculation, twice a week until the $28^{th}$ day. Wherein the triangle-dotted line is the control group, the square-dotted line is the IgG antibody group, and the rhombus-dotted line is ABCG2-PKU1 antibody group. In the experiment comparing the antitumor effects of the three antibodies ABCG2-PKU1, ABCG2-PKU1-1 and ABCG2-PKU2, lung cancer non-resistant cells A549 was inoculated in the left axilla, $5 \times 10^6$/mouse. When the diameter of the tumor reached 5 mm, on the $9^{th}$ day, the nude mice were randomly divided into 5 groups: one control group, ABCG2 antibody (commercial antibody BXP-21) group, ABCG2-PKU1 antibody group, ABCG2-PKU1-1 antibody group, and ABCG2-PKU2 antibody group. For antibody treatment, the mice were given a dose of 0.3 mg/kg for 3 days×6 via tail vein injection. The size of the tumor was measured with a caliper, once/3 days, until the $30^{th}$ day. The nude mice were sacrificed.

The result is as shown in FIG. 10. In the experiment of tumor formation in nude mice, the drug was administered one week after the formation of tumor, the dose was 0.3 mg/kg, once a week for three weeks. One control group, one IgG antibody-administrated group and one ABCG2-PKU1 antibody-administrated group were set in FIG. 10A. Compared with the control group without administration and the IgG group, the ABCG2-PKU1 antibody group could significantly reduce the size of the transplanted tumor. The nude mice in FIG. 10B were inoculated with 5×10⁶ lung cancer cells, and tumor volume was measured from the 4$^{th}$ day of inoculation, twice a week until the 28$^{th}$ days. Wherein the triangle-dotted line is the control group, the square-dotted line is the IgG antibody group, and the rhombus-dotted line is the ABCG2-PKU1 antibody group.

In the experiment of comparing the antitumor effect of the three ABCG2 antibodies prepared in Example 3, lung cancer non-resistant cell A549 was inoculated in the left axilla, 5×10⁶/mouse. When the diameter of the tumor reached 5 mm on the 9$^{th}$ day, the nude mice were randomly divided into 5 groups: control group, ABCG2 antibody (commercial product) group, ABCG2-PKU1 antibody group, ABCG2-PKU1-1 antibody group, and ABCG2-PKU2 antibody group. Antibody treatment was given via tail vein injection for 3 days×6 at a dose of 0.3 mg/kg. The size of the tumor was measured with a caliper, once every 3 days, until the 30$^{th}$ day. The nude mice were sacrificed. FIG. 10C shows that all the tumor volume reduced with varying degrees after antibody treatment compared with the control group. In FIG. 10D, the line is the control group, the dotted line is the ABCG2 antibody group, the square-dotted line is the ABCG2-PKU1 antibody group, the short-dashed line is the ABCG2-PKU1-1 body group, and the dashed-dotted line is the ABCG2-PKU2 antibody group.

Conclusion: Compared with the control group without treatment, ABCG2 antibody group, the ABCG2-PKU1 antibody group and the ABCG2-PKU2 antibody group, the ABCG2-PKU1-1 antibody group has the strongest effect on reducing the volume of transplanted tumor, the ABCG2-PKU1 antibody group ranks second, the ABCG2 and ABCG2-PKU2 antibody groups are relatively worse. ABCG2-PKU1-1 antibody has the best inhibitory effect on the tumor formation of lung cancer A549 cell in nude mice. The possible mechanism may be that, this antibody can target CSCs and mesenchymal stem cells that highly express ABCG2 protein, by inhibiting the self-renewal of CSCs and the tumor microenvironment formed by mesenchymal stem cells, thereby inhibits tumor growth.

Example 7: Determination of Variable Region Sequence of ABCG2 Monoclonal Antibody 1. Confirmation of Variable Region Sequence of Monoclonal Antibody Produced by Hybridoma CGMCC12653

1-1. Total mRNA was extracted from the hybridoma cell line under accession number CGMCC12653 Light chain primers IgG$_K$-VF: TATTGGATCCATGAAGTTGCCTGTT (SEQ ID NO: 4) and IgG$_K$-VR: TTACTCGAGAG-GAACATGTGTACTTTG (SEQ ID NO: 5) were used; conditions for PCR: 94° C., 5 min; 94° C., 30 sec, 55° C., 30 sec, 72° C., 40 sec for a total of 38 cycles; 72° C., 10 min; 4° C. The amplified fragment was sequenced.

The light chain variable region sequence of the ABCG2 antibody produced by the hybridoma cell CGMCC12653 was identified by IgBLAST as:

```
                                          (SEQ ID NO: 2)
GAAGTTGTGATGGCCCAAACTCCACTCTCCCTGCCTGTCAGTCTTGGAGA

TCAAGCCTCCATCTCTTGCAGATCTAGTCAGAGCCTTGTACAAGGTGATG

GAAACACCTATTTACATTGGTATCTGCAGAAGCCAGGCCAGTCTCCAAAG

CTCCTGATCTACAAAGTTTCTAACCGATTTTCTGGGGTCCCAGAGAGGTT

CAGTGGCAGTGGATCAGGGACAGATTTCACACTCAAGATCAGCAGAGTGG

AGGCTGAGGATCTGGGACTTTATTTCTGTTCTCAAAGTACACATGTTCCT

C
```

1-2. Heavy chain primers IgGH-VF: TTGGATC-CATGGGATGGAGCTG TATCATCC (SEQ ID NO: 6) and IgGH-VR: TACTCGAGGCTGAGC TGCATGTAGGCGT (SEQ ID NO: 7) were used; conditions for PCR: 94° C., 5 min; 94° C., 30 sec, 58° C., 30 sec, 72° C., 40 sec for 38 cycles; 72° C., 10 min; 4° C., ∞. The amplified fragment was sequenced. The heavy chain variable region sequence of anti-ABCG2 antibody produced by hybridoma cell CGMCC12653 was identified by IgBLAST as:

(SEQ ID NO: 3)
CAGGTCCAACTGCAGCAGCCTGGGGCTGAACTTGTGATGCCTGGGACTTC

AGTGAAGATGTCCTGTAAGGCATCTGGGTACACATTCACTGACTACTGGC

TGCACTGGGTGACACAGAGGCCTGGACAAGGCCTTGCGTGGATCGGAACG

ATTGATACTTCTGATGGTTATACTAGGTACAATCAAAACTTCCAGGGCAA

GGCCACATTGACTGTAGACACTTCCTCCAGTAC-GCCTACATGCAGCTCA

GCCTCAGTAAAGGGCAATTCTGCAG

2. Confirmation of Variable Region Sequence of Monoclonal Antibody Produced by Hybridoma CGMCC14683

The method was the same as described for sequencing the variable region of the monoclonal antibody produced by accession number CGMCC12653, except that the primer for sequencing was changed.

2-1. Total mRNA was extracted from the hybridoma cell line under accession number CGMCC14683. Light chain primers IgG$_K$-VF: TATTGGATCCATGAAGTTGCCTGTT (SEQ ID NO: 4) and IgG$_K$-VR: TTACTCGAGAG-GAACATGTGTACTTTG (SEQ ID NO: 5) were used; conditions for PCR: 94° C., 5 min; 94° C., 30 sec, 55° C., 30 sec, 72° C., 40 sec for a total of 38 cycles; 72° C., 10 min; 4° C. The amplified fragment was sequenced.

The light chain variable region sequence of the ABCG2 antibody produced by the hybridoma cell CGMCC14683 was identified by IgBLAST as:

(SEQ ID NO: 11)
GAAGTTGTGATGGCCCAAACTCCACTCTCCCTGCCTGTCAGTCTTGGAGA

TCAAGCCTCCATCTCTTGCAGATCTAGTCAGAGCCTTGTACAAGGTGATG

GAAACACCTATTTACATTGGTATCTGCAGAAGCCAGGCCAGTCTCCAAAG

CTCCTGATCTACAAAGTTTCTAACCGATTTTCTGGGGTCCCAGAGAGGTT

CACTGGCACTGGATCAGGGACAGATTTCACACTCAAGATCAGCAGAGTGG

AGGCTGAGGATCTGGGACTTTATTTCTGTTCTCAAAGTACACATGTTCCT

C 2-2. Heavy chain primers IgGH-VF: TTGGATC-CATGGGATGGAGCTGTATCATCC (SEQ ID NO: 6) and IgGH-VR: CAGCTGGGAAGGTGTGCAC (SEQ ID NO: 10) were used; conditions for PCR: 94° C., 5 min; 94° C., 30 sec, 58° C., 30 sec, 72° C., 40 sec for 38 cycles; 72° C., 10 min; 4° C., ∞. The amplified fragment was sequenced. The heavy chain variable region sequence of the ABCG2 antibody produced by hybridoma cell CGMCC14683 was identified by IgBLAST as:

(SEQ ID NO: 12)
CAGGTCCAACTGCAGCAGCCTGGGGCTGAACTTGTGATGCCTGGGACTT

CAGTGAAGATGTCCTGTAAGGCATCTGGGTACACATTCACTGACTACTG

GCTGCACTGGGTGACACAGAGGCCTGGACAAGGCCTTGCGTGGATCGGA

ACGATTGATACTTCTGATGGTTATACTAGGTACAATCAAAACTTCCAGG

GCAAGGCCACATTGACTGTAGACACTTCCTCCAGTACAGCCTTCATGCG

GCTCAGCAGCCTGACATCTGAGGACTCTGCGGTCTATTACTGTACAAGA

TCGGAGAGGGGAATTCCTATGGACTACTGGGGTCAAGGAACCTCACTCA

TCGTCTCCTCAG

3. The amino acid sequences of the ABCG2 antibodies produced by the hybridoma cell numbered CGMCC12653 and CGMCC14683 were obtained based on the above-identified ABCG2 antibody variable region gene sequence.

The light chain variable region of the hybridoma cell numbered CGMCC12653 is:

(SEQ ID NO: 8)
EVVMAQTPLSLPVSLGDQASISCRSSQSLVQGDGNTYLHWYLQKPGQSPK

LLIYKVSNRFSGVPERFSGSGSGTDFTLKISRVEAEDLGLYFCSQSTHVP

The heavy chain variable region of the hybridoma cell numbered CGMCC12653 is:

(SEQ ID NO: 9)
QVQLQQPGAELVMPGTSVKMSCKASGYTFTDYWLHWVTQRPGQGLAWIGT

IDTSDGYTRYNQNFQGKATLTVDTSSSTPTCSSA

The light chain variable region of the hybridoma cell numbered CGMCC12653 is identical to the light chain variable region produced by CGMCC14683 and is:

(SEQ ID NO: 8)
EVVMAQTPLSLPVSLGDQASISCRSSQSLVQGDGNTYLHWYLQKPGQSPKL

LIYKVSNRFSGVPERFSGSGSGTDFTLKISRVEAEDLGLYFCSQSTHVP and CDRL1, CDRL2 and CDRL3 are set forth in SEQ ID NOs: 14, 15 and 16, respectively.

The heavy chain variable region of the hybridoma cell numbered CGMCC14683 is:

(SEQ ID NO: 13)
QVQLQQPGAELVMPGTSVKMSCKASGYTFTDYWLHWVTQRPGQGLAWIGTI

DTSDGYTRYNQNFQGKATLTVDTSSSTAFMRLSSLTSEDSAVYYCTRSERG

IPMDYWGQGTSLIVSS and CDRH1, CDRH2 and CDRH3 are set forth in SEQ ID NOs: 17, 18 and 19, respectively.

Sequence Annotation:
1. Antigenic polypeptide sequence, No. 1
2. K chain gene sequence, No. 2
3. H chain gene sequence, No. 3
4. K chain variable region amplification primer F, No. 4
5. K chain variable region amplification primer R, No. 5
6. H chain variable region amplification primer F, No. 6
7. H chain variable region amplification primer R, No. 7
8. ABCG2-PKU1 antibody light chain variable region amino acid sequence, No. 8
9. ABCG2-PKU1 antibody heavy chain variable region amino acid sequence, No. 9

Above are the primers, gene and amino acid sequences related to ABCG2-PKU1 antibody.

10. H chain variable region amplification primer R, No. 10
11. ABCG2-PKU1-1 antibody light chain variable region gene sequence, No. 11
12. ABCG2-PKU1-1 antibody heavy chain variable region gene sequence, No. 12
13. ABCG2-PKU1-1 antibody heavy chain variable region amino acid sequence, No. 13

These four are the primer, gene and amino acid sequences related to ABCG2-PKU1-1 antibody.

Example 8: Construction and Function Detection of scFv of ABCG2 Monoclonal Antibody The heavy chain variable region sequence and the light chain variable region sequence of two monoclonal antibodies were obtained according to Example 7. Following the literatures (Rohatgi S, Ganju P, Sehgal D. Systematic design and testing of nested (RT-) PCR primers for specific amplification of mouse rearranged/expressed immunoglobulin variable region genes from small number of B cells. J Immunol Methods. 2008 Dec. 31; 339(2):205-19. doi: 10.1016/j.jim.2008.09.017, Zhou H, Fisher R J, Papas T S. Optimization of primer sequences for mouse scFv repertoire display library construction. Nucleic Acids Res. 1994 Mar. 11; 22(5):888-9 and WANG Hong, CHEN Dan, DENG Ning, XIANG Jun-jian, JIN Ying-jie, HUANG Hong-Jiang, TANG Yong, YANG Hong-yu, Cloning of the variable region genes from hybridoma against bFGF and expression of single chain antibody fragments in E. coli HB2151. Chin J Cell Mol hnnmnol 2007.23(12), 1150-1153), splice-overlap extension (SOE) PCR was used to construct scFv. First, the upstream and downstream primers ($V_L$-F, $V_L$-R) of the light chain variable region and the upstream and downstream primers ($V_H$-F, $V_H$-R) of the heavy chain variable region were designed, 12 bases of H chain hinge region were added to the 5' end of the downstream primer of the heavy chain variable region, which is complementary to the upstream of the linker. The region overlapping with the linker was added to the 5' of the upstream primer of the light chain variable region. $V_L$-R and linker were used as primers, the recovered $V_L$ gene fragment was purified to be a template, and a $V_L$-liner fragment was obtained by PCR amplification. Then $V_H$-F and $V_L$-R were used as primers, the recovered $V_H$ gene fragment and $V_L$-liner fragment were purified to be templates, and a $V_H$-liner-$V_L$ structured gene fragment was obtained by SOE PCR amplification. The purified recovered scFv gene fragment was inserted into a T vector and then transformed into E. coli DH5α competent cells. 4 clones were picked for PCR identification and double enzyme digestion, and the positive bacterial clone was subjected to sequencing. The scFv gene fragment and the pCANTAB 5E vector, of which the sequencing results were correct, were subjected to double enzyme digestion with SfiI and Not I. The digested fragment was ligated to pCANTAB 5E-scFv expression vector by T4 DNA ligase. The vector was expressed in prokaryotic system and induced by IPTG, and active scFv was detected in both the supernatant and the periplasmic extract. It was confirmed by indirect ELISA method that the expressed antibody had a specific activity of binding to ABCG2, and its biological activity was similar to that of the parental ABCG2 monoclonal antibody, and its biological activity could achieve 50% of the biological activity of the antibody secreted by the hybridoma cells.

What is claimed is:

1. An anti-ABCG2 monoclonal antibody comprising:
a CDRL1, a CDRL2, and a CDRL3 in a light chain variable region, and
a CHRH1, a CDRH2, and a CDRH3 in a heavy chain variable region,
wherein the CDRL1, CDRL2 and CDRL3 have an amino acid sequence set forth in SEQ ID NOs: 14, 15 and 16, respectively, and
wherein the CDRH1, CDRH2 and CDRH3 have an amino acid sequence set forth in SEQ ID NOs: 17, 18 and 19, respectively.

2. A hybridoma deposited with an accession number of CGMCC14683 on Sep. 5, 2017, at China General Microbiological Culture Collection Center with an address of No. 1 Courtyard, Beichen West Road, Chaoyang District, Beijing, China.

3. The anti-ABCG2 monoclonal antibody according to claim 1,
comprising a heavy chain variable region with a sequence set forth in SEQ ID NO: 13 and a light chain variable region with a sequence set forth in SEQ ID NO: 8.

4. The anti-ABCG2 monoclonal antibody according to claim 1, which is coupled to an anticancer drug, wherein the anticancer drug may be one or more selected from the group consisting of cisplatin, doxorubicin, mitoxantrone, 5-fluorouracil, temozolomide and flavopiridol.

5. The anti-ABCG2 monoclonal antibody according to claim 1, which is an engineered antibody.

6. The anti-ABCG2 monoclonal antibody according to claim 3, which is a humanized antibody.

7. The anti-ABCG2 monoclonal antibody according to claim 3, which is further engineered with another cancer therapeutic drug.

8. A method of treating a cancer, comprising administering the monoclonal antibody according to claim 1, wherein the cancer is selected from the group consisting of lung cancer, breast cancer, colon cancer, liver cancer, pancreatic cancer, glioma, gastric cancer, bladder cancer, cervical cancer, prostate cancer, ovarian cancer, chorionic epithelioma, malignant teratoma and leukemia, and lung cancer resistant to cisplatin, breast cancer resistant to doxorubicin, flavopiridol, 5-fluorouracil and mitoxantrone, and colon cancer resistant to flavopiridol and mitoxantrone.

9. The method according to claim 8, further comprising administering another cancer therapeutic drug in combination.

10. The method according to claim 8, wherein the cancer is lung cancer.

* * * * *

SEQUENCE LISTING

```
<160> NUMBER OF SEQ ID NOS: 19

<210> SEQ ID NO 1
<211> LENGTH: 15
<212> TYPE: PRT
<213> ORGANISM: Mus musculus
<220> FEATURE:
<221> NAME/KEY: Antigen Amino Acid Sequence
<222> LOCATION: (1)..(15)

<400> SEQUENCE: 1

Thr Gly Glu Glu Tyr Leu Val Lys Gln Gly Ile Asp Leu Ser Pro
1               5                   10                  15

<210> SEQ ID NO 2
<211> LENGTH: 301
<212> TYPE: DNA
<213> ORGANISM: Mus musculus
<220> FEATURE:
<221> NAME/KEY: Light Chain Variable Region
<222> LOCATION: (1)..(301)

<400> SEQUENCE: 2
gaagttgtga tggcccaaac tccactctcc ctgcctgtca gtcttggaga tcaagcctcc      60
atctcttgca gatctagtca gagccttgta caaggtgatg gaaacaccta tttacattgg     120
tatctgcaga agccaggcca gtctccaaag ctcctgatct acaaagtttc taaccgattt     180
tctggggtcc cagagaggtt cagtggcagt ggatcaggga cagatttcac actcaagatc     240
agcagagtgg aggctgagga tctgggactt tatttctgtt ctcaaagtac acatgttcct     300
c                                                                    301

<210> SEQ ID NO 3
<211> LENGTH: 274
<212> TYPE: DNA
<213> ORGANISM: Mus musculus
```

```
<220> FEATURE:
<221> NAME/KEY: Heavy Chain Variable Region
<222> LOCATION: (1)..(274)

<400> SEQUENCE: 3
caggtccaac tgcagcagcc tggggctgaa cttgtgatgc ctgggacttc agtgaagatg      60
tcctgtaagg catctgggta cacattcact gactactggc tgcactgggt gacacagagg     120
cctggacaag gccttgcgtg gatcggaacg attgatactt ctgatggtta ctactaggtac    180 aatcaaaact tccagggcaa ggccacattg actgtagaca cttcctccag tacgcctaca     240
tgcagctcag cctcagtaaa gggcaattct gcag                                 274

<210> SEQ ID NO 4
<211> LENGTH: 25
<212> TYPE: DNA
<213> ORGANISM: Artificial
<220> FEATURE:
<223> OTHER INFORMATION: Light Chain Variable Region Primer 1?? IgG??-VF

<400> SEQUENCE: 4
tattggatcc atgaagttgc ctgtt                                            25

<210> SEQ ID NO 5
<211> LENGTH: 27
<212> TYPE: DNA
<213> ORGANISM: Artificial
<220> FEATURE:
<223> OTHER INFORMATION: Light Chain Variable Region Primer 2?? IgG??-VR

<400> SEQUENCE: 5
ttactcgaga ggaacatgtg tactttg                                          27

<210> SEQ ID NO 6
<211> LENGTH: 30
<212> TYPE: DNA
<213> ORGANISM: Artificial
<220> FEATURE:
<223> OTHER INFORMATION: Heavy Chain Variable Region Primer??IgGH-VF

<400> SEQUENCE: 6
ttggatccat gggatggagc tgtatcatcc                                       30

<210> SEQ ID NO 7
<211> LENGTH: 28
<212> TYPE: DNA
<213> ORGANISM: Artificial
<220> FEATURE:
<223> OTHER INFORMATION: Heavy Chain Variable Region Primer??IgGH-VR

<400> SEQUENCE: 7
tactcgaggc tgagctgcat gtaggcgt                                         28

<210> SEQ ID NO 8
<211> LENGTH: 100
<212> TYPE: PRT
<213> ORGANISM: Mus musculus
<220> FEATURE:
<221> NAME/KEY: Light Chain Variable Region Amino Acid Sequence
<222> LOCATION: (1)..(100)

<400> SEQUENCE: 8

Glu Val Val Met Ala Gln Thr Pro Leu Ser Leu Pro Val Ser Leu Gly
1               5                   10                  15

Asp Gln Ala Ser Ile Ser Cys Arg Ser Ser Gln Ser Leu Val Gln Gly
```

```
                20                  25                  30

Asp Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Glu Arg Phe Ser Gly Ser Gly Ser Gly Thr Asp Phe Thr Leu Lys Ile
 65                  70                  75                  80

Ser Arg Val Glu Ala Glu Asp Leu Gly Leu Tyr Phe Cys Ser Gln Ser
                85                  90                  95

Thr His Val Pro
            100

<210> SEQ ID NO 9
<211> LENGTH: 84
<212> TYPE: PRT
<213> ORGANISM: Mus musculus
<220> FEATURE:
<221> NAME/KEY: Heavy Chain Variable Region Amino Acid Sequence
<222> LOCATION: (1)..(84)

<400> SEQUENCE: 9

Gln Val Gln Leu Gln Gln Pro Gly Ala Glu Leu Val Met Pro Gly Thr
 1               5                  10                  15

Ser Val Lys Met Ser Cys Lys Ala Ser Gly Tyr Thr Phe Thr Asp Tyr
            20                  25                  30

Trp Leu His Trp Val Thr Gln Arg Pro Gly Gln Gly Leu Ala Trp Ile
        35                  40                  45

Gly Thr Ile Asp Thr Ser Asp Gly Tyr Thr Arg Tyr Asn Gln Asn Phe
 50                  55                  60

Gln Gly Lys Ala Thr Leu Thr Val Asp Thr Ser Ser Ser Thr Pro Thr
 65                  70                  75                  80

Cys Ser Ser Ala

<210> SEQ ID NO 10
<211> LENGTH: 19
<212> TYPE: DNA
<213> ORGANISM: Artificial
<220> FEATURE:
<223> OTHER INFORMATION: Heavy Chain Variable Region Primer??IgGH-VF

<400> SEQUENCE: 10
cagctgggaa ggtgtgcac                                                   19

<210> SEQ ID NO 11
<211> LENGTH: 301
<212> TYPE: DNA
<213> ORGANISM: Mus musculus
<220> FEATURE:
<221> NAME/KEY: Light Chain Variable Region
<222> LOCATION: (1)..(301)

<400> SEQUENCE: 11
gaagttgtga tggcccaaac tccactctcc ctgcctgtca gtcttggaga tcaagcctcc       60
atctcttgca gatctagtca gagccttgta caaggtgatg aaacacccta tttacattgg     120
tatctgcaga agccaggcca gtctccaaag ctcctgatct acaaagtttc taaccgattt     180
tctggggtcc cagagaggtt cagtggcagt ggatcaggga cagatttcac actcaagatc     240
agcagagtgg aggctgagga tctgggactt tatttctgtt ctcaaagtac acatgttcct     300
c                                                                    301
```

<210> SEQ ID NO 12
<211> LENGTH: 355
<212> TYPE: DNA
<213> ORGANISM: Mus musculus
<220> FEATURE:
<221> NAME/KEY: Heavy Chain Variable Region
<222> LOCATION: (1)..(355)

<400> SEQUENCE: 12

```
caggtccaac tgcagcagcc tggggctgaa cttgtgatgc ctgggacttc agtgaagatg      60
tcctgtaagg catctgggta cacattcact gactactggc tgcactgggt gacacagagg     120
cctggacaag gccttgcgtg gatcggaacg attgatactt ctgatggtta tactaggtac     180
aatcaaaact tccagggcaa ggccacattg actgtagaca cttcctccag tacagccttc     240
atgcggctca gcagcctgac atctgaggac tctgcggtct attactgtac aagatcggag     300
agggaattc ctatggacta ctggggtcaa ggaacctcac tcatcgtctc ctcag           355
```

<210> SEQ ID NO 13
<211> LENGTH: 118
<212> TYPE: PRT
<213> ORGANISM: Mus musculus
<220> FEATURE:
<221> NAME/KEY: Heavy Chain Variable Region Amino Acid Sequence
<222> LOCATION: (1)..(118)

<400> SEQUENCE: 13

```
Gln Val Gln Leu Gln Gln Pro Gly Ala Glu Leu Val Met Pro Gly Thr
1               5                   10                  15
Ser Val Lys Met Ser Cys Lys Ala Ser Gly Tyr Thr Phe Thr Asp Tyr
            20                  25                  30
Trp Leu His Trp Val Thr Gln Arg Pro Gly Gln Gly Leu Ala Trp Ile
        35                  40                  45
Gly Thr Ile Asp Thr Ser Asp Gly Tyr Thr Arg Tyr Asn Gln Asn Phe
    50                  55                  60
Gln Gly Lys Ala Thr Leu Thr Val Asp Thr Ser Ser Ser Thr Ala Phe
65                  70                  75                  80
Met Arg Leu Ser Ser Leu Thr Ser Glu Asp Ser Ala Val Tyr Tyr Cys
                85                  90                  95
Thr Arg Ser Glu Arg Gly Ile Pro Met Asp Tyr Trp Gly Gln Gly Thr
            100                 105                 110
Ser Leu Ile Val Ser Ser
        115
```

<210> SEQ ID NO 14
<211> LENGTH: 11
<212> TYPE: PRT
<213> ORGANISM: Artificial
<220> FEATURE:
<223> OTHER INFORMATION: CDRL1

<400> SEQUENCE: 14

```
Gln Ser Leu Val Gln Gly Asp Gly Asn Thr Tyr
1               5                   10
```

<210> SEQ ID NO 15
<211> LENGTH: 3
<212> TYPE: PRT
<213> ORGANISM: Artificial
<220> FEATURE:
<223> OTHER INFORMATION: CDRL2

```
<400> SEQUENCE: 15

Lys Val Ser
1

<210> SEQ ID NO 16
<211> LENGTH: 7
<212> TYPE: PRT
<213> ORGANISM: Artificial
<220> FEATURE:
<223> OTHER INFORMATION: CDRL3

<400> SEQUENCE: 16

Ser Gln Ser Thr His Val Pro
1               5

<210> SEQ ID NO 17
<211> LENGTH: 8
<212> TYPE: PRT
<213> ORGANISM: Artificial
<220> FEATURE:
<223> OTHER INFORMATION: CDRH1

<400> SEQUENCE: 17

Gly Tyr Thr Phe Thr Asp Tyr Trp
1               5

<210> SEQ ID NO 18
<211> LENGTH: 8
<212> TYPE: PRT
<213> ORGANISM: Artificial
<220> FEATURE:
<223> OTHER INFORMATION: CDRH2

<400> SEQUENCE: 18

Ile Asp Thr Ser Asp Gly Tyr Thr
1               5

<210> SEQ ID NO 19
<211> LENGTH: 11
<212> TYPE: PRT
<213> ORGANISM: Artificial
<220> FEATURE:
<223> OTHER INFORMATION: CDRH3

<400> SEQUENCE: 19

Thr Arg Ser Glu Arg Gly Ile Pro Met Asp Tyr
1               5                   10
```